(12) United States Patent
Gurge et al.

(10) Patent No.: US 9,949,919 B2
(45) Date of Patent: Apr. 24, 2018

(54) STABLE, NON-IRRITATING TOPICAL FORMULATIONS OF HYDROQUINONE

(71) Applicant: SHAMROC, INC., Carlsbad, CA (US)

(72) Inventors: Ronald M. Gurge, Franklin, MA (US); Mark W. Trumbore, Westford, MA (US); Nupoor Devrajbhai Hirani, Lincoln, RI (US)

(73) Assignee: SHAMROC, INC., Carlsbad, CA (US)

( * ) Notice: Subject to any disclaimer, the term of this patent is extended or adjusted under 35 U.S.C. 154(b) by 0 days.

(21) Appl. No.: 14/747,781

(22) Filed: Jun. 23, 2015

(65) Prior Publication Data
US 2015/0290121 A1    Oct. 15, 2015

Related U.S. Application Data

(62) Division of application No. 13/778,696, filed on Feb. 27, 2013, now Pat. No. 9,089,506.

(51) Int. Cl.
| | | |
|---|---|---|
| *A61K 8/97* | (2017.01) | |
| *A61K 8/64* | (2006.01) | |
| *A61Q 19/02* | (2006.01) | |
| *A61K 8/36* | (2006.01) | |
| *A61K 8/42* | (2006.01) | |
| *A61Q 19/00* | (2006.01) | |
| *A61K 8/49* | (2006.01) | |
| *A61K 8/60* | (2006.01) | |
| *A61K 8/34* | (2006.01) | |
| *A61K 8/67* | (2006.01) | |
| *A61K 8/9706* | (2017.01) | |

(52) U.S. Cl.
CPC ............... *A61K 8/97* (2013.01); *A61K 8/342* (2013.01); *A61K 8/345* (2013.01); *A61K 8/347* (2013.01); *A61K 8/36* (2013.01); *A61K 8/42* (2013.01); *A61K 8/494* (2013.01); *A61K 8/498* (2013.01); *A61K 8/4946* (2013.01); *A61K 8/602* (2013.01); *A61K 8/64* (2013.01); *A61K 8/675* (2013.01); *A61K 8/9706* (2017.08); *A61Q 19/00* (2013.01); *A61Q 19/02* (2013.01); *A61K 2800/75* (2013.01)

(58) Field of Classification Search
CPC .... A61K 2800/75; A61K 8/342; A61K 8/345; A61K 8/347; A61K 8/36; A61K 8/42; A61K 8/494; A61K 8/4946; A61K 8/498; A61K 8/602; A61K 8/64; A61K 8/675; A61K 8/97; A61K 8/975; A61Q 19/00; A61Q 19/02
See application file for complete search history.

(56) References Cited

U.S. PATENT DOCUMENTS

| | | | |
|---|---|---|---|
| 6,335,023 B1 | 1/2002 | Yu et al. | |
| 6,551,604 B1 * | 4/2003 | Beck | ........................ A61K 8/29 424/401 |
| 9,089,506 B2 | 7/2015 | Gurge et al. | |
| 2006/0182794 A1 * | 8/2006 | Modi | ................... A61K 8/0291 424/450 |
| 2006/0263309 A1 * | 11/2006 | Bissett | ..................... A61K 8/35 424/59 |
| 2008/0181920 A1 * | 7/2008 | Buerger | ................... A61K 8/27 424/401 |
| 2008/0275118 A1 * | 11/2008 | Shaw | ..................... A61K 8/355 514/559 |

* cited by examiner

*Primary Examiner* — Sreeni Padmanabhan
*Assistant Examiner* — Jody Karol
(74) *Attorney, Agent, or Firm* — Procopio Cory Hargreaves and Savitch LLP; Pattric J. Rawlins

(57) ABSTRACT

Described herein are methods and compositions for increasing the efficacy and decreasing the irritancy of topical formulations of hydroquinone.

12 Claims, 4 Drawing Sheets

Figure 1

| Ingredient | Wt / Wt % | |
|---|---|---|
| | NB1238-21 | NB1164-57 |
| Purified Water | 53.165 | 53.08 |
| Hydrofluorocarbon 227ea | 12.5 | 12.5 |
| Pentylene Glycol | 5.3 | 5.3 |
| Cyclomethicone | 5.0 | 1.5 |
| Niacinamide | 4 | 4 |
| Isononyl Isononoate | 2.5 | 2 |
| C12-C15 Alkyl Ethylhexanoate | 2.5 | 2 |
| Glycerin | 2.175 | 2.175 |
| Hydroquinone | 2 | 2 |
| Alpha-Arbutin | 2 | 2 |
| Dimethicone/Divinyldimethicone/Silsesquioxane Crosspolymer | 2 | 1.75 |
| Moringa Oleifera Seed Oil | 2 | N.P.* |
| Glyceryl Stearate | 1.69 | 1.69 |
| Cetyl Alcohol | 1.69 | 1.69 |
| Dimethicone | 1.25 | 1 |
| Cetearyl Alcohol | 1 | 1 |
| Kojic Acid | 1 | 1 |
| Panthenol | 1 | 1 |
| 1-Methylhydantoine-2-Imide | 1 | 1 |
| Algae Extract and Mugwort (Artemisia vulgaris) Extract | 1 | 1 |
| Magnesium Aluminum Silicate | 1 | 1 |
| PEG-75 Stearate | 0.875 | 0.875 |
| Avena Sativa (Oat) Kernel Extract | <1 | <1 |
| Saccharomyces/Xylinum/Black Tea Ferment | 0.44 | 2.65 |
| Palmaria Palmata Extract | 0.3 | 0.3 |
| Brassica Napus Extract | 0.075 | 0.075 |
| Punica Granatum (Pomegranate) Seed Oil | 0.3 | 0.625 |
| Rubus Occidentalis (Black Raspberry) Seed Oil | 0.3 | 0.625 |
| Vaccinium Macrocarpon (Cranberry) Seed Oil | 0.3 | 0.625 |
| Citrullus Lanatus (Watermelon) Seed Oil | < 0.05 | < 0.125 |
| Rubus Idaeus (Raspberry) Seed Oil | < 0.05 | < 0.125 |
| Salvia Hispanica (Chia) Seed Oil | < 0.05 | < 0.125 |
| Tetrahexadecyl Ascorbate | 0.5 | 0.5 |
| Ceteth-20 | 0.37 | 0.37 |
| Steareth-20 | 0.37 | 0.37 |
| Allantoin | 0.49 | 0.49 |
| Chlorphenesin | 0.3 | 0.3 |
| Hexapeptide-2 | <1 | <1 |
| Jojoba Esters | 0.25 | N.P.* |
| Moringa Oil/Hydrogenated Moringa Oil Esters | 0.25 | N.P.* |
| Bisabolol | 0.2 | 0.2 |
| Fragrance | 0.2 | 0.2 |
| Sodium Bisulfite | 0.05 | 0.05 |
| Sodium Sulfite | 0.05 | 0.05 |

Figure 1, continued

| Tocopheryl Acetate | 0.1 | 0.5 |
|---|---|---|
| Xanthan Gum | 0.1 | 0.1 |
| Citric Acid | 0.15 | 0.15 |
| Potassium Sorbate | 0.15 | 0.15 |
| Sodium Benzoate | 0.15 | 0.15 |
| Dextran | <1 | <1 |
| Sodium Hyaluronate | 0.01 | 0.01 |
| BHT | 0.2 | 0.2 |
| Stearyl Glycyrrhetinate | 0.1 | 0.1 |
| Disodium EDTA | 0.1 | 0.1 |
| Phenoxyethanol | <0.1 | <0.1 |
| Hydroxyethylcellulose | <1 | <1 |
| Glycyrrhiza Glabra (Licorice) Root Extract | 0.05 | 0.05 |
| Acacia Decurrens/Jojoba/Sunflower Seed Wax Polyglyceryl-3 Esters | N.P.* | 2 |
| Butyrospermum Parkii (Shea) Butter | N.P.* | 2 |

Figure 2

| Efficacy Attributes | Week 4 | | Week 8 | | Week 12 | |
|---|---|---|---|---|---|---|
| | 4% HQ | 2% HQ | 4% HQ | 2% HQ | 4% HQ | 2% HQ |
| Overall Photodamage | 48.48 | 53.03 | 81.36 | 84.75 | 88.89 | 93.65 |
| Mottled Pigmentation | 69.70 | 69.70 | 89.83 | 89.83 | 93.65 | 98.41 |
| Erythema | 28.79 | 24.24 | 42.37 | 40.68 | 44.44 | 46.03 |
| Visual Texture | 43.94 | 36.36 | 69.49 | 69.49 | 85.71 | 85.71 |
| Fine Lines | 25.76 | 24.24 | 38.98 | 37.29 | 39.68 | 39.68 |
| Improved Color | 59.09 | 60.61 | 86.44 | 88.14 | 95.24 | 98.41 |

Figure 3

| Efficacy Attributes | Week 4 | | Week 8 | | Week 12 | |
|---|---|---|---|---|---|---|
| | 4% HQ | 2% HQ | 4% HQ | 2% HQ | 4% HQ | 2% HQ |
| Overall Photodamage | 8.74 | 9.37 | 16.78 | 17.22 | 22.63 | 21.49 |
| Mottled Pigmentation | 14.20 | 13.18 | 24.43 | 23.10 | 30.23 | 28.02 |
| Erythema | 6.15 | 2.19 | 7.76 | 6.91 | 12.26 | 12.13 |
| Visual Texture | 8.49 | 7.92 | 15.01 | 15.08 | 21.78 | 20.32 |
| Fine Lines | 5.22 | 4.51 | 9.25 | 7.96 | 9.71 | 8.82 |
| Improved Color | 12.20 | 11.68 | 22.82 | 20.08 | 28.63 | 26.55 |

Figure 4

| Week 2 | | Week 4 | | Week 8 | | Week 12 | |
|---|---|---|---|---|---|---|---|
| 4% HQ | 2% HQ | 4% HQ | 2% HQ | 4% HQ | 2% HQ | 4% HQ | 2% HQ |
| 22.73% | 31.82% | 22.73% | 18.18% | 25.00% | 15.00% | 19.05% | 14.29% |

Figure 5

| Week 2 | | Week 4 | | Week 8 | | Week 12 | |
|---|---|---|---|---|---|---|---|
| 4% HQ | 2% HQ | 4% HQ | 2% HQ | 4% HQ | 2% HQ | 4% HQ | 2% HQ |
| 0.227 | 0.364 | 0.318 | 0.227 | 0.350 | 0.250 | 0.238 | 0.190 |

Figure 6

| Week 2 | | Week 4 | | Week 8 | | Week 12 | |
|---|---|---|---|---|---|---|---|
| 4% HQ | 2% HQ | 4% HQ | 2% HQ | 4% HQ | 2% HQ | 4% HQ | 2% HQ |
| 86.36% | 86.36% | 100.00% | 100.00% | 100.00% | 100.00% | 100.00% | 100.00% |

Figure 7

| Time Point | 30° C | 40° C |
|---|---|---|
| Initial | 99.5% | 99.5% |
| 1 Month | 101.6% | 100.8% |

STABLE, NON-IRRITATING TOPICAL FORMULATIONS OF HYDROQUINONE

CROSS-REFERENCE

This Application is a divisional of U.S. application Ser. No. 13/778,696 filed Feb. 27, 2013, entitled "Stable, Non-Irritating Topical Formulations Of Hydroquinone", the entire contents of which are hereby incorporated by reference herein.

BACKGROUND

The efficacy of a topically applied drug or cosmetic is strongly dependent upon the constituents of the product vehicle. In addition, many active ingredients in drug and cosmetic formulations have limited chemical stability and are inherently irritating. For example, formulations containing the skintone-evening active hydroquinone are inherently irritating and chemically unstable.

SUMMARY OF THE INVENTION

In certain embodiments, the invention relates to a method for increasing the efficacy of a hydroquinone-containing formulation comprising the step of
adding an activating agent to the continuous phase of the formulation, wherein the formulation comprises an oil-in-water emulsion, thereby forming an improved hydroquinone-containing formulation.

In certain embodiments, the invention relates to a method for decreasing the irritancy of a hydroquinone-containing formulation comprising the step of
adding an emollient and an anti-irritant to the formulation, wherein the formulation comprises an oil-in-water emulsion, thereby forming a less irritating hydroquinone-containing formulation.

In certain embodiments, the invention relates to a method comprising the steps of:
combining, in a first container, BHT, stearyl glycyrrhetinate, cetyl alcohol, ceteth-20, steareth-20, glyceryl stearate, PEG-75 stearate, cetostearyl alcohol, *jojoba* esters, isonoyl isononanoate, $C_{12}$-$C_{15}$ alkyl ethylhexanoate, *moringa* butter, *moringa* oil, tocopheryl acetate, tetrahexadecyl ascorbate, bisabolol, dimethicone, dimethicone/divinyldimethicone/silsesquioxane crosspolymer, black raspberry seed oil, cranberry seed oil, pomegranate seed oil, watermelon seed oil, raspberry seed oil, and chia seed oil, thereby forming mixture A;
in a second container, adding, while homogenizing, magnesium aluminum silicate to water, thereby forming mixture B;
homogenizing mixture B;
in a third container, combining pentylene glycol and xanthan gum, thereby forming mixture C;
adding, in the second container, mixture C to mixture B, thereby forming mixture BC;
adding to mixture BC in the second container allantoin, sodium hyaluronate, panthenol, potassium sorbate, sodium benzoate, disodium EDTA, citric acid, and niacinamide, thereby forming mixture BCD.
adding to mixture BCD mixture A, thereby forming mixture ABCD;
adding to mixture ABCD algae extract, mugwort (*Artemisia vulgaris*) extract, water, glycerin, and *avena sativa* (Oat) kernel extract, thereby forming mixture E;
dissolving sodium bisulfite and sodium sulfite in water, thereby forming solution F;
adding solution F to mixture E, thereby forming mixture EF;
combining pentylene glycol and chlorphenesin, thereby forming mixture G;
adding mixture G to mixture EF, thereby forming mixture EFG;
adding to mixture EFG water, dextran, and hexapeptide-2, thereby forming mixture H;
combining water, pentylene glycol, and alpha-arbutin, thereby forming mixture I;
adding mixture I to mixture H, thereby forming mixture HI;
combining water, pentylene glycol, and kojic acid, thereby forming mixture J;
adding mixture J to mixture HI, thereby forming mixture HIJ;
adding to mixture HIJ cyclomethicone, water, glycerin, *brassica napus* extract, *palmaria palmata* extract, *saccharomyces/xylinum*/black tea ferment, and 1-methylhydantoine-2-imide, thereby forming mixture K;
combining pentylene glycol and licorice root extract, thereby forming mixture L;
adding mixture L to mixture K, thereby forming mixture KL;
combining pentylene glycol, water and hydroquinone, thereby forming mixture M; and
adding mixture M to mixture KL, thereby forming a hydroquinone-containing formulation.

BRIEF DESCRIPTION OF THE FIGURES

FIG. 1 tabulates the components and weight percentages of various formulations of the invention. *N.P.=not present.

FIG. 2 tabulates the percentage of subjects showing improvement from baseline when treated with a formulation of the invention (2% HQ) or a commercial product (4% HQ).

FIG. 3 tabulates the average percent improvement versus baseline for subjects treated with a formulation of the invention (2% HQ) or a commercial product (4% HQ).

FIG. 4 tabulates the percentage of subjects reporting irritation when treated with a formulation of the invention (2% HQ) or a commercial product (4% HQ).

FIG. 5 tabulates the average irritation rating for subjects treated with a formulation of the invention (2% HQ) or a commercial product (4% HQ).

FIG. 6 tabulates the percentage of subjects rating as "good" or higher their overall satisfaction with use of a formulation of the invention (2% HQ) or a commercial product (4% HQ).

FIG. 7 tabulates the percent recovery of hydroquinone from a formulation of the invention (2% HQ) after storage for a month at 30° C./65% relative humidity or 45° C./75% relative humidity.

DETAILED DESCRIPTION OF THE INVENTION

Overview

In certain embodiments, the invention relates to a method for improving the efficacy and chemical stability of a topical hydroquinone containing formulation while controlling its irritancy. In certain embodiments, the invention relates to a method for doubling the efficacy of hydroquinone containing topical formulations by the addition of activating agents to the continuous phase of an oil-in-water emulsion-based formulation while improving chemical stability. In certain embodiments, the invention relates to the surprising discovery that systematic variation in the oil phase constituents allows specific tailoring of the aesthetic attributes of the formulation without negatively affecting product efficacy. In certain embodiments, the invention relates to the surprising discovery that incorporation of anti-irritant ingredients in both the continuous and discontinuous phases allows for control of irritation in an otherwise inherently irritating product.

In certain embodiments, formulations made by methods of the invention comprise a high-viscosity oil-in-water emulsion containing greater than 20% oil phase components and less than 55% water. In certain embodiments, the product can be packaged into aerosol cans and pressurized with hydrofluorocarbon propellants, or packaged into airless pumps. In certain embodiments, when an aerosol can is actuated, a dense, time- and temperature-stable foam is dispensed. In certain embodiments, formulations dispensed from either an aerosol can or an airless pump contain hydroquinone and are suitable for evening skintone, color, and pigmentation via topical application. In certain embodiments, the formulations are chemically stable, well-tolerated, exhibit minimal irritation, are easily spread over large areas of body surface, and are rapidly absorbed without leaving a sticky residue.

In certain embodiments, the invention relates to a formulation comprising, by weight of the formulation, about 4.0%-about 10.0% surfactants/co-surfactants, about 10.0%-about 19.0% emollients, about 5.5%-about 9.5%/o humectants, about 0.7%-about 2.0% thickeners, about 0.5%-about 3.5% preservatives, about 8.5%-about 14.5% activating agents, about 0.5%-about 3.5% anti-irritants and about 50.0%-about 60.0% water. In certain embodiments, the invention relates to a formulation comprising, by weight of the formulation, the surfactants/co-surfactants cetearyl alcohol (about 0.5-about 1.5%), cetyl alcohol (about 1.2%-about 2.2%), glyceryl stearate (about 1.2%-about 2.2%), ceteth-20 (about 0.2%-about 0.6%), steareth-20 (about 0.2%-about 0.6%), PEG-75 stearate (about 0.25%-about 1.25%), and polyglyceryl-3 esters of *Acacia* decurrens/*jojoba*/Sunflower Seed wax (about 0-about 4.0%). In certain embodiments, the invention relates to a formulation comprising, by weight of the formulation, the emollients cyclomethicone (about 0.5%-about 6.0%), isononyl isononoate (about 1.5%-3.0%). $C_{12}$-$C_{15}$ alkyl ethylhexanoate (about 1.5%-about 3.0%), dimethicone/divinyldimethicone/silsesquioxane crosspolymer (about 1.25%-about 2.5%), *moringa oleifera* seed oil (about 0-about 3.0%), dimethicone (about 0.5%-about 1.75%), *punica granatum* (pomegranate) seed oil (about 0.1%-about 1.0%), *rubus occidentalis* (black raspberry) seed oil (about 0.1%-about 1.0%), *vaccinium macrocarpon* (cranberry) seed oil (about 0.1%-about 1.0%), *citrullus lanatus* (watermelon) seed oil (about 0.005%-about 0.5%), *rubus idacus* (raspberry) seed oil (about 0.005%-about 0.5%). *salvia hispanica* (chia) seed oil (about 0.005%-about 0.5%), *jojoba* esters (about 0-about 0.5%), *moringa* oil/hydrogenated *morninga* oil esters (about 0-about 0.5%), and *butyrospermum parkii* (shea) butter (about 0-about 4.0%). In certain embodiments, the invention relates to a formulation comprising, by weight of the formulation, the humectants pentylene glycol (about 4.3%-about 6.3%), glycerin (about 1.2%-about 3.2%), and sodium Hyaluronate (about 0.005%-about 0.015%); the thickeners magnesium aluminum silicate (about 0.5%-about 1.5%), xanthan gum (about 0.05%-about 0.15%), dextran (about 0.05%-about 1.0%), and hydroxyethylcellulose (about 0.05%-about 1.0%); and the preservatives chlorphenesin (about 0.15%-about 0.45%), sodium bisulfite (about 0.025%-about 0.075%), sodium sulfite (about 0.025%-about 0.075%), tocopheryl acetate (about 0.05%-about 0.75%), citric acid (about 0.1%-about 0.2%), potassium sorbate (about 0.1%-about 0.2%), sodium benzoate (about 0.1%-about 0.2%), BHT (about 0.15%-about 0.25%), disodium EDTA (about 0.05%-about 0.15%), and phenoxyethanol (about 0.01%-about 0.1%). In certain embodiments, the invention relates to a formulation comprising, by weight of the formulation, the anti-irritation ingredients panthenol (about 0.5%-about 1.5%), *avena sativa* (oat) kernel extract (about 0.05%-about 1.0%), allantoin (about 0.25%-about 0.75%), bisabolol (about 0.1%-about 0.3%), and stearyl glycyrrhetinate (about 0.05%-about 1.5%). In certain embodiments, the invention relates to a formulation comprising, by weight of the formulation, the activating agents niacinamide (about 2.0%-6.0%), alpha-arbutin (about 1.0%-about 3.0%), kojic acid (about 0.5%-about 1.5%), 1-methylhydantoine-2-imide (about 0.5%-about 1.5%), algae extract/mugwort (*Artemisia vulgaris*) extract (about 0.5%-about 1.5%), *saccharomyces/xylinum*/black tea ferment (about 0.2%-about 3.5%), *palmaria* palmate extract (about 0.2%-about 0.4%), *brassica napus* extract (about 0.05%-about 0.1%), hexapeptide-2 (about 0.001%-about 1.0%), and *glycyrrhiza glabra* (licorice) root extract (about 0.025%-about 0.075%).

Definitions

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion. i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one. B, with no A present (and optionally including elements other than A); in yet another embodiment, to at least one, optionally including more than one. A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Exemplary Constituents of Emulsions and Compositions of the Invention

Exemplary identities of various constituents of the compositions of the present invention are described below.

1. Propellants

In certain embodiments, the propellant is a HFA or a mixture of one or more hydrofluorocarbons. Suitable hydrofluorocarbons include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. The concentration of the HFA propellant is about 2% to about 50% by weight of the composition. In certain embodiments, the propellant comprises a hydrofluoroolefin (HFO), or a mixture of HFO and HFA. Suitable hydrofluoroolefins include 1,3,3,3-tetrafluoropropene (HFO 1234ze) and mixtures and admixtures of this and other HFO suitable for topical use. The concentration of the HFO propellant is about 2% to about 50% by weight of the composition. Hydrocarbon as well as CFC propellants can also be used in the present invention.

2. Vehicles

Suitable topical vehicles and vehicle components for use with the formulations of the invention are well known in the cosmetic and pharmaceutical arts, and include such vehicles (or vehicle components) as water, organic solvents such as alcohols (particularly lower alcohols readily capable of evaporating from the skin such as ethanol), glycols (such as propylene glycol, butylene glycol, and glycerol (glycerin)), aliphatic alcohols (such as lanolin); mixtures of water and organic solvents (such as water and alcohol), and mixtures of organic solvents such as alcohol and glycerol (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, dimethiconol, dimethicone, and dimethicone copolyol; hydrocarbon-based materials such as petrolatum and squalane; and other vehicles and vehicle components that are suitable for administration to the skin, as well as mixtures of topical vehicle components as identified above or otherwise known to the art.

In one embodiment, the compositions of the present invention are oil-in-water emulsions. Liquids suitable for use in formulating compositions of the present invention include water, and water-miscible solvents, such as glycols (e.g., ethylene glycol, butylene glycol, isoprene glycol, propylene glycol), glycerol, liquid polyols, dimethyl sulfoxide, and isopropyl alcohol. One or more aqueous vehicles may be present.

In one embodiment, formulations without methanol, ethanol, propanols, or butanols are desirable.

3. Surfactants and Emulsifiers

Many topical formulations contain chemical emulsions which use surface active ingredients (emulsifiers and surfactants) to disperse dissimilar chemicals in a particular solvent system. For example, most lipid-like (oily or fatty) or lipophilic ingredients do not uniformly disperse in aqueous solvents unless they are first combined with emulsifiers, which form microscopic aqueous soluble structures (droplets) that contain a lipophilic interior and a hydrophilic exterior, resulting in an oil-in-water emulsion. In order to be soluble in aqueous media, a molecule must be polar or charged so as to favorably interact with water molecules, which are also polar. Similarly, to dissolve an aqueous-soluble polar or charged ingredient in a largely lipid or oil-based solvent, an emulsifier is typically used which forms stable structures that contain the hydrophilic components in the interior of the structure while the exterior is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion droplet. Emulsion destabilization results in the aqueous and lipophilic ingredients separating into two layers, potentially destroying the commercial value of a topical product.

Surfactants suitable for use in the present invention may be ionic or non-ionic. These include, but are not limited to: sodium isostearate, cetyl alcohol, polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20. Brij S10 (polyethylene glycol octadecyl ether, average $M_n \sim 711$), PEG-20 phytosterol, and Poloxamers (including, but not limited to, Poloxamer 188 ($HO(C_2H_4O)_a(CH(CH_3)CH_2O)_b(C_2H_4O)_aH$, average molecular weight 8400) and Poloxamer 407 ($HO(C_2H_4O)_a(CH(CH_3)CH_2O)_b(C_2H_4O)_aH$, wherein a is about 101 and b is about 56)). Appropriate combinations or mixtures of such surfactants may also be used according to the present invention.

Many of these surfactants may also serve as emulsifiers in formulations of the present invention.

Other suitable emulsifiers for use in the formulations of the present invention include, but are not limited to, *glycine soja* protein, sodium lauroyl lactylate, polyglyceryl-4 diisostearate-polyhydroxystearate-sebacate, behentrimonium methosulfate-cetearyl alcohol, non-ionic emulsifiers like emulsifying wax, polyoxyethylene oleyl ether, PEG-40 stearate, carbomer, cetostearyl alcohol (cetearyl alcohol), ceteareth-12, ceteareth-20, ceteareth-25, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, laureth-12, steareth-2, and steareth-20, or combinations/mixtures thereof, as well as cationic emulsifiers like stearamidopropyl dimethylamine and behentrimonium methosulfate, or combinations/mixtures thereof.

4. Moisturizers, Emollients, and Humectants

One of the most important aspects of topical products in general, and cosmetic products in particular, is the consumer's perception of the aesthetic qualities of a product. For example, while white petrolatum is an excellent moisturizer and skin protectant, it is rarely used alone, especially on the face, because it is greasy, sticky, does not rub easily into the skin and may soil clothing. Consumers highly value products which are aesthetically elegant and have an acceptable tactile feel and performance on their skin.

Suitable moisturizers for use in the formulations of the present invention include, but are not limited to, lactic acid and other hydroxy acids and their salts, glycerol, propylene glycol, butylene glycol, sodium PCA, sodium hyaluronate, Carbowax 200, Carbowax 400, and Carbowax 800.

Suitable emollients or humectants for use in the formulations of the present invention include, but are not limited to, panthenol, cetyl palmitate, glycerol (glycerin), PPG-15 stearyl ether, lanolin alcohol, lanolin, lanolin derivatives, cholesterol, petrolatum, isostearyl neopentanoate, octyl stearate, mineral oil, isocetyl stearate, myristyl myristate, octyl dodecanol, 2-ethylhexyl palmitate (octyl palmitate), dimethicone, phenyl trimethicone, cyclomethicone, $C_{12}$-$C_{15}$ alkyl benzoates, dimethiconol, propylene glycol, *Theobroma grandiflorum* seed butter, sunflower seed oil, ceramides (e.g., ceramide 2 or ceramide 3), hydroxypropyl bispalmitamide MEA, hydroxypropyl bislauramide MEA, hydroxypropyl bisisostearamide MEA, 1,3-bis(N-2-(hydroxyethyl)stearoylamino)-2-hydroxy propane, bis-hydroxyethyl tocopheryluccinoylamido hydroxypropane, urea, aloe, allantoin, glycyrrhetinic acid, safflower oil, oleyl alcohol, oleic acid, stearic acid, dicaprylate/dicaprate, diethyl sebacate, isostearyl alcohol, pentylene glycol, isononyl isononanoate, polyquaternium-10 (quaternized hydroxyethyl cellulose), *camellia oleifera* leaf extract, phytosteryl canola glycerides, shea butter, caprylic/capric triglycerides, *punica granatum* sterols, ethylhexyl stearate, betaine, behenyl alcohol (docosanol), stearyl alcohol (1-octadecanol), *laminaria ochroleuca* extract, behenic acid, caproyl sphingosine, caproyl phytosphingosine, dimethicone-divinyldimethicone-silsesquioxane crosspolymer, potassium lactate, sodium hyaluronate crosspolymer, hydrolyzed hyaluronic acid, sodium butyroyl-formoyl hyaluronate, polyglutamic acid, tetradecyl aminobutyroylvalylaminobutyric urea trifluoroacetate, *micrococcus lysate*, hydrolyzed rice bran protein, *glycine soja* protein, and 1,3-bis(N-2-(hydroxyethyl)palmitoylamino)-2-hydroxypropane.

In addition, appropriate combinations and mixtures of any of these moisturizing agents and emollients may be used in accordance with the present invention. Many of these are classified as "skin conditioners."

5. Preservatives and Antioxidants

The composition may further include components adapted to improve the stability or effectiveness of the applied formulation.

Suitable preservatives for use in the present invention include, but are not limited to: ureas, such as imidazolidinyl urea and diazolidinyl urea; chlorphenesin; methylisothiazolinone; phenoxyethanol; sodium methyl paraben, methylparaben, ethylparaben, and propylparaben; ethylhexyl glycerin; potassium sorbate; sodium benzoate; sorbic acid; benzoic acid; caprylyl glycol; formaldehyde; phytosphingosine; citric acid; sodium citrate; zinc citrate; chlorine dioxide; quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; piroctone olamine; *Vitis vinifera* seed oil; and alcoholic agents, for example, chlorobutanol, dichlorobenzyl alcohol, phenylethyl alcohol, and benzyl alcohol.

Suitable antioxidants include, but are not limited to, ascorbic acid and its esters, sodium bisulfite, butylated hydroxytoluene (BHT), butylated hydroxyanisole, tocopherols (such as α-tocopherol), tocopheryl acetate, superoxide dismutase, oxidoreductases, *Arabidopsis thaliana* extract, chrysin, black raspberry seed oil, raspberry seed oil, pomegranate seed oil, cranberry seed oil, sodium ascorbate/ascorbic acid, ascorbyl palmitate, propyl gallate, and chelating agents like EDTA (e.g., disodium EDTA), citric acid, and sodium citrate.

In certain embodiments, the antioxidant or preservative comprises (3-(4-chlorophenoyx)-2-hydroxypropyl)carbamate.

In certain embodiments, antioxidants or preservatives of the present invention may also function as a moisturizer or emollient, for example.

In addition, combinations or mixtures of these preservatives or anti-oxidants may also be used in the formulations of the present invention.

6. Active Agents

The active agent may be any material that has a desired effect when applied topically to a mammal, particularly a human. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones. Mixtures of any of these active agents may also be employed. Additionally, dermatologically-acceptable salts and esters of any of these agents may be employed.

7. Purging Gases

In one embodiment, the air in the container charged with the composition is replaced by an inert gas. In certain embodiments, the inert gas is selected from the group consisting of argon, nitrogen, and mixtures thereof.

8. Buffer Salts

Suitable buffer salts are well-known in the art. Examples of suitable buffer salts include, but are not limited to sodium citrate, citric acid, sodium phosphate monobasic, sodium phosphate dibasic, sodium phosphate tribasic, potassium phosphate monobasic, potassium phosphate dibasic, and potassium phosphate tribasic.

9. Viscosity Modifiers

Suitable viscosity adjusting agents (i.e., thickening and thinning agents or viscosity modifying agents) for use in the formulations of the present invention include, but are not limited to, protective colloids or non-ionic gums such as hydroxyethylcellulose, xanthan gum, and *sclerotium* gum, as well as magnesium aluminum silicate, silica, microcrystalline wax, beeswax, paraffin, and cetyl palmitate. Crosspolymers of acrylates/$C_{10-30}$ alkyl acrylate are also considered. In addition, appropriate combinations or mixtures of these viscosity adjusters may be utilized according to the present invention.

10. Additional Constituents

Additional constituents suitable for incorporation into the emulsions of the present invention include, but are not limited to: skin protectants, adsorbents, demulcents, emollients, moisturizers, sustained release materials, solubilizing agents, skin-penetration agents, skin soothing agents, deodorant agents, antiperspirants, sun screening agents, sunless tanning agents, vitamins, hair conditioning agents, anti-irritants, anti-aging agents, abrasives, absorbents, anti-caking agents, anti-static agents, astringents (e.g., witch hazel, alcohol, and herbal extracts such as chamomile extract), binders/excipients, buffering agents, chelating agents, film forming agents, conditioning agents, opacifying agents, lipids, immunomodulators, and pH adjusters (e.g., citric acid, sodium hydroxide, and sodium phosphate).

For example, lipids normally found in healthy skin (or their functional equivalents) may be incorporated into the emulsions of the present invention. In certain embodiments, the lipid is selected from the group consisting of ceramides, cholesterol, and free fatty acids. Examples of lipids include, but are not limited to, ceramide 1, ceramide 2, ceramide 3, ceramide 4, ceramide 5, ceramide 6, hydroxypropyl bispalmitamide MEA, and hydroxypropyl bislauramide MEA, and combinations thereof.

Examples of peptides that interact with protein structures of the dermal-epidermal junction include palmitoyl dipeptide-5 diaminobutyloyl hydroxythreonine, palmitoyl tripeptide-5, acetyl octapeptide-3, pentapeptide-3, palmitoyl dipeptide-5 diaminohydroxybutyrate, dipeptide diaminobutyroyl benzylamide diacetate, palmitoyl tetrapeptide-7, palmitoyl oligopeptide, and palmitoyl dipeptide-6 diaminohydroxybutyrate.

Examples of skin soothing agents or anti-irritants include, but are not limited to algae extract, mugwort extract, stearyl glycyrrhetinate, bisabolol allantoin, aloe, avocado oil, green tea extract, hops extract, chamomile extract, colloidal oatmeal, calamine, cucumber extract, and combinations thereof.

N-hydroxysuccinimide activates the elimination of blood originated pigments responsible for dark color and inflammation that causes under eye circles.

In certain embodiments, the compositions comprise bergamot or bergamot oil. Bergamot oil is a natural skin toner and detoxifier. In certain embodiments, it may prevent premature aging of skin and may have excellent effects on oily skin conditions and acne.

Examples of vitamins include, but are not limited to, vitamins A, D, E, K, and combinations thereof. Vitamin analogues are also contemplated; for example, the vitamin D analogues calcipotriene or calcipotriol.

In certain embodiments, the vitamin may be present as tetrahexyldecyl ascorbate. This compound exhibits anti-oxidant activity, inhibiting lipid peroxidation. In certain embodiments, use can mitigate the damaging effects of UV exposure. Studies have shown it to stimulate collagen production as well as clarifying and brightening the skin by inhibiting melanogenesis (the production of pigment) thereby promoting a more even skin tone.

Examples of sunscreens include, but are not limited to, p-aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide, 4-methylbenzylidene camphor, methylene bis-benzotriazolyl tetramethylbutylphenol, bis-ethylhexyloxyphenol methoxyphenyl triazine, terephthalylidene dicamphor sulfonic acid, drometrizole trisiloxane, disodium phenyl dibenzimidazole tetrasulfonate, diethylamino hydroxybenzoyl hexyl benzoate, octyl triazone, diethylhexyl butamido triazone, polysilicone-15, and combinations thereof.

Suitable fragrances and colors may be used in the formulations of the present invention. Examples of fragrances and colors suitable for use in topical products are known in the art.

Suitable immunomodulators include, but are not limited to, beta-glucan.

In certain embodiments, palmitoyl-lysyl-valyl-lysine bis-trifluoroacetate is added. This peptide stimulates collagen synthesis in human fibroblasts.

In certain embodiments, plant extracts may be included. Examples include *artemisia vulgaris* extract, plankton extract, chlorella vulgaris extract, and phytosterol.

An example of a film-forming agent is polysilicone-11.

Often, one constituent of a composition may accomplish several functions. In one embodiment, the present invention relates to constituents that may act as a lubricant, an emollient, or a skin-penetrating agent. In one embodiment, the multi-functional constituent is socetyl stearate, isopropyl isostearate, isopropyl palmitate, or isopropyl myristate.

Exemplary Formulations of the Invention

In certain embodiments, the invention relates to a formulation comprising, by weight of the formulation, hydroquinone,
about 4.0%-about 10.0% surfactants/co-surfactants,
about 10.0%-about 19.0% emollients.
about 5.5%-about 9.5% humectants,
about 0.7%-about 2.0% thickeners,
about 0.5%-about 3.5% preservatives,
about 8.5%-about 14.5% activating agents,
about 0.5%-about 3.5% anti-irritants, and
about 50.0%-about 60.0% water.

In certain embodiments, the invention relates to any one of the aforementioned formulations, wherein the formulation is an improved hydroquinone-containing formulation or a less irritating hydroquinone-containing formulation.

In certain embodiments, the invention relates to any one of the aforementioned formulations, wherein the surfactants are selected from the group consisting of ceteth-20 and steareth-20, and the co-surfactants are selected from the group consisting of cetyl alcohol, glyceryl stearate. PEG-75 stearate, cetearyl alcohol, and polyglyceryl-3 esters of *acacia* decurrens/*jojoba*/sunflower seed wax.

In certain embodiments, the invention relates to any one of the aforementioned formulations, wherein the concentration of ceteth-20 is from about 0.2%-about 0.6%.

In certain embodiments, the invention relates to any one of the aforementioned formulations, wherein the concentration of steareth-20 is from about 0.2%-about 0.6%.

In certain embodiments, the invention relates to any one of the aforementioned formulations, wherein the concentration of cetearyl alcohol is from about 0.5%-about 1.5%.

In certain embodiments, the invention relates to any one of the aforementioned formulations, wherein the concentration of cetyl alcohol is from about 1.2%-about 2.2%.

In certain embodiments, the invention relates to any one of the aforementioned formulations, wherein the concentration of glyceryl stearate is from about 1.2%-about 2.2%.

In certain embodiments, the invention relates to any one of the aforementioned formulations, wherein the concentration of PEG-75 stearate is from about 0.25%-about 1.25%.

In certain embodiments, the invention relates to any one of the aforementioned formulations, wherein the concentration of polyglyceryl-3 esters of *acacia* decurrens/*jojoba*/sunflower seed wax is from about 0-about 4.0%.

In certain embodiments, the invention relates to any one of the aforementioned formulations, wherein the emollients are selected from the group consisting of cyclomethicone, isononyl isononoate, $C_{12}$-$C_{15}$ alkyl ethylhexanoate, dimethicone/divinyldimethicone/silsesquioxane crosspolymer, *moringa oleifera* seed oil, dimethicone, *punica granatum* seed oil, *rubus occidentalis* seed oil, *vaccinium macrocarpon* seed oil, *citrullus lanatus* seed oil, *rubus idaeus* seed oil, *salvia hispanica* seed oil. *jojoba* esters. *moringa* oil/hydrogenated *moringa* oil esters, and *butyrospermum parkii* butter.

In certain embodiments, the invention relates to any one of the aforementioned formulations, wherein the concentration of cyclomethicone is from about 0.5%-about 6.0%.

In certain embodiments, the invention relates to any one of the aforementioned formulations, wherein the concentration of isononyl isononoate is from about 1.5%-about 3.0%.

In certain embodiments, the invention relates to any one of the aforementioned formulations, wherein the concentration of $C_{12}$-$C_{15}$ alkyl ethylhexanoate is from about 1.5%-about 3.0%.

In certain embodiments, the invention relates to any one of the aforementioned formulations, wherein the concentration of dimethicone/divinyldimethicone/silsesquioxane crosspolymer is from about 1.25%-about 2.5%.

In certain embodiments, the invention relates to any one of the aforementioned formulations, wherein the concentration of *moringa oleifera* seed oil is from about 0-about 3.0%.

In certain embodiments, the invention relates to any one of the aforementioned formulations, wherein the concentration of dimethicone is from about 0.5%-about 1.75%.

In certain embodiments, the invention relates to any one of the aforementioned formulations, wherein the concentration of *punica granatum* seed oil is from about 0.1%-about 1.0%.

In certain embodiments, the invention relates to any one of the aforementioned formulations, wherein the concentration of *rubus occidentalis* seed oil is from about 0.1%-about 1.0%.

In certain embodiments, the invention relates to any one of the aforementioned formulations, wherein the concentration of *vaccinium macrocarpon* seed oil is from about 0.1%-about 1.0%.

In certain embodiments, the invention relates to any one of the aforementioned formulations, wherein the concentration of *citrullus lanatus* seed oil is from about 0.005%-about 0.5%.

In certain embodiments, the invention relates to any one of the aforementioned formulations, wherein the concentration of *rubus idaeus* seed oil is from about 0.005%-about 0.5%.

In certain embodiments, the invention relates to any one of the aforementioned formulations, wherein the concentration of *salvia hispanica* seed oil is from about 0.005%-about 0.5%.

In certain embodiments, the invention relates to any one of the aforementioned formulations, wherein the concentration of *jojoba* esters is from about 0-about 0.5%.

In certain embodiments, the invention relates to any one of the aforementioned formulations, wherein the concentration of *moringa* oil/hydrogenated *moringa* oil esters is from about 0-about 0.5%.

In certain embodiments, the invention relates to any one of the aforementioned formulations, wherein the concentration of *butyrospermum parkii* butter is from about 0-about 4.0%.

In certain embodiments, the invention relates to any one of the aforementioned formulations, wherein the humectants are selected from the group consisting of pentylene glycol, glycerin, and sodium hyaluronate.

In certain embodiments, the invention relates to any one of the aforementioned formulations, wherein the thickeners are selected from the group consisting of magnesium aluminum silicate, xanthan gum, dextran, and hydroxyethylcellulose.

In certain embodiments, the invention relates to any one of the aforementioned formulations, wherein the preservatives are selected from the group consisting of chlorphenesin, sodium bisulfite, sodium sulfite, tocopheryl acetate, citric acid, potassium sorbate, sodium benzoate, BHT, disodium EDTA, and phenoxyethanol.

In certain embodiments, the invention relates to any one of the aforementioned formulations, wherein the anti-irritants are selected from the group consisting of panthenol, *avena sativa* kernel extract, allantoin, bisabolol, and stearyl glycyrrhetinate.

In certain embodiments, the invention relates to any one of the aforementioned formulations, wherein the activating agents are selected from the group consisting of niacinamide, alpha-arbutin, kojic acid, 1-methylhydantoine-2-imide, algae/mugwort extract, *saccharomyces*/*xylinum*/black tea ferment, *palmaria* palmate extract, *brassica napus* extract, hexapeptide-2, and *glyerrhiza glabra* root extract.

In certain embodiments, the invention relates to any one of the aforementioned formulations, wherein the concentration of niacinamide is from about 2.0%-about 6.0%.

In certain embodiments, the invention relates to any one of the aforementioned formulations, wherein the concentration of alpha-arbutin is from about 1.0%-about 3.0%.

In certain embodiments, the invention relates to any one of the aforementioned formulations, wherein the concentration of kojic acid is from about 0.5%-about 1.5%.

In certain embodiments, the invention relates to any one of the aforementioned formulations, wherein the concentration of 1-methylhydantoine-2-imide is from about 0.5%-about 1.5%.

In certain embodiments, the invention relates to any one of the aforementioned formulations, wherein the concentration of algae/mugwort extract is from about 0.5%-about 1.5%.

In certain embodiments, the invention relates to any one of the aforementioned formulations, wherein the concentration of *saccharomyces/xylinum*/black tea ferment is from about 0.2%-about 3.5%.

In certain embodiments, the invention relates to any one of the aforementioned formulations, wherein the concentration of *palmaria* palmate extract is from about 0.2%-about 0.4%.

In certain embodiments, the invention relates to any one of the aforementioned formulations, wherein the concentration of *brassica napus* extract is from about 0.05%-about 0.1%.

In certain embodiments, the invention relates to any one of the aforementioned formulations, wherein the concentration of hexapeptide-2 is from about 0.001%-about 1.0%.

In certain embodiments, the invention relates to any one of the aforementioned formulations, wherein the concentration of *glycyrrhiza glabra* root extract is from about 0.025%-about 0.075%.

In certain embodiments, the invention relates to any one of the aforementioned formulations, wherein the anti-irritants are selected from the group consisting of panthenol, *avena sativa* kernel extract, allantoin, bisabolol, and stearyl glycyrrhetinate.

In certain embodiments, the invention relates to any one of the aforementioned formulations, wherein the emollients are selected from the group consisting of *punica granatum* seed oil, *rubus occidentalis* seed oil, *vaccinium macrocarpon* seed oil, *citrullus lanatus* seed oil, *rubus idaeus* seed oil, and *salvia hispanica* seed oil.

In certain embodiments, the invention relates to any one of the aforementioned formulations, wherein the concentration of panthenol seed oil is from about 0.5%-about 1.5%.

In certain embodiments, the invention relates to any one of the aforementioned formulations, wherein the concentration of *avena sativa* kernel extract is from about 0.05%-about 1.0%.

In certain embodiments, the invention relates to any one of the aforementioned formulations, wherein the concentration of allantoin is from about 0.25%-about 0.75%.

In certain embodiments, the invention relates to any one of the aforementioned formulations, wherein the concentration of bisabolol is from about 0.1%-about 0.3%.

In certain embodiments, the invention relates to any one of the aforementioned formulations, wherein the concentration of stearyl glycyrrhetinate is from about 0.05%-about 1.5%.

In certain embodiments, the invention relates to any one of the aforementioned formulations, wherein the concentration of *punica granatum* seed oil is from about 0.1%-about 1.0%.

In certain embodiments, the invention relates to any one of the aforementioned formulations, wherein the concentration of *rubus occidentalis* seed oil is from about 0.1%-about 1.0%.

In certain embodiments, the invention relates to any one of the aforementioned formulations, wherein the concentration of *vaccinium macrocarpon* seed oil is from about 0.1%-about 1.0%.

In certain embodiments, the invention relates to any one of the aforementioned formulations, wherein the concentration of *citrullus lanatus* seed oil is from about 0.005%-about 0.5%.

In certain embodiments, the invention relates to any one of the aforementioned formulations, wherein the concentration of *rubus idaeus* seed oil is from about 0.005%-about 0.5%.

In certain embodiments, the invention relates to any one of the aforementioned formulations, wherein the concentration of *salvia hispanica* seed oil is from about 0.005%-about 0.5%.

In certain embodiments, the invention relates to a formulation comprising
Purified Water
Hydrofluorocarbon 227ea
Pentylene Glycol
Cyclomethicone
Niacinamide
Isononyl Isononoate
C12-C15 Alkyl Ethylhexanoate
Glycerin
Hydroquinone
Alpha-Arbutin
Dimethicone/Divinyldimethicone/Silsesquioxane Crosspolymer
Glyceryl Stearate
Cetyl Alcohol
Dimethicone
Cetearyl Alcohol
Kojic Acid
Panthenol
1-Methylhydantoine 2-Imide
Algae Extract and Mugwort (*Artemisia vulgaris*) Extract
Magnesium Aluminum Silicate
PEG-75 Stearate
*Avena Sativa* (Oat) Kernel Extract
*Saccharomyces/Xylinum*/Black Tea Ferment
*Palmaria Palmata* Extract
*Brassica Napus* Extract
*Punica Granatum* (Pomegranate) Seed Oil
*Rubus Occidentalis* (Black Raspberry) Seed Oil
*Vaccinium Macrocarpon* (Cranberry) Seed Oil
*Citrullus Lanatus* (Watermelon) Seed Oil
*Rubus Idaeus* (Raspberry) Seed Oil
*Salvia Hispanica* (Chia) Seed Oil
Tetrahexadecyl Ascorbate
Ceteth-20
Steareth-20
Allantoin
Chlorphenesin
Hexapeptide-2
Bisabolol
Sodium Bisulfite
Sodium Sulfite
Tocopheryl Acetate
Xanthan Gum
Citric Acid
Potassium Sorbate
Sodium Benzoate
Dextran
Sodium Hyaluronate
BHT
Stearyl Glycyrrhetinate
Disodium EDTA Phenoxyethanol
Hydroxyethylcellulose
*Glycyrrhiza Glabra* (Licorice) Root Extract In certain embodiments, the invention relates to formulation consisting essentially of
Purified Water
Hydrofluorocarbon 227ea
Pentylene Glycol
Cyclomethicone
Niacinamide
Isononyl Isononoate
C12-C15 Alkyl Ethylhexanoate
Glycerin
Hydroquinone
Alpha-Arbutin
Dimethicone/Divinyldimethicone/Silsesquioxane Crosspolymer
Glyceryl Stearate
Cetyl Alcohol
Dimethicone
Cetearyl Alcohol
Kojic Acid
Panthenol
1-Methylhydantoine-2-Imide
Algae Extract and Mugwort (*Artemisia vulgaris*) Extract
Magnesium Aluminum Silicate
PEG-75 Stearate
*Avena Sativa* (Oat) Kernel Extract
*Saccharomyces/Xylinum*/Black Tea Ferment
*Palmaria Palmata* Extract
*Brassica Napus* Extract
*Punica Granatum* (Pomegranate) Seed Oil
*Rubus Occidentalis* (Black Raspberry) Seed Oil
*Vaccinium Macrocarpon* (Cranberry) Seed Oil
*Citrullus Lanatus* (Watermelon) Seed Oil
*Salvia Hispanica* (Chia) Seed Oil
Tetrahexadecyl Ascorbate
Ceteth-20
Steareth-20
Allantoin
Chlorphenesin
Hexapeptide-2
Bisabolol
Fragrance
Sodium Bisulfite
Sodium Sulfite
Tocopheryl Acetate
Xanthan Gum
Citric Acid
Potassium Sorbate
Sodium Benzoate
Dextran
Sodium Hyaluronate
BHT
Stearyl Glycyrrhetinate
Disodium EDTA
Phenoxyethanol
Hydroxyethylcellulose
*Glycyrrhiza Glabra* (Licorice) Rout Extract In certain embodiments, the invention relates to a formulation comprising
Purified Water
Hydrofluorocarbon 227ea
Pentylene Glycol
Cyclomethicone
Niacinamide
Isononyl Isononoate
C12-C15 Alkyl Ethylhexanoate
Glycerin
Hydroquinone
Alpha-Arbutin
Dimethicone/Divinyldimethicone/Silsesquioxane Crosspolymer
*Moringa Oleifera* Seed Oil
Glyceryl Stearate
Cetyl Alcohol
Dimethicone
Cetearyl Alcohol
Kojic Acid
Panthenol
1-Methylhydantoine-2-Imide
Algae Extract and Mugwort (*Artemisia vulgaris*) Extract
Magnesium Aluminum Silicate
PEG-75 Stearate
*Avena Sativa* (Oat) Kernel Extract
*Saccharomyces/Xylinum*/Black Tea Ferment
*Palmaria Palmata* Extract
*Brassica Napus* Extract
*Punica Granatum* (Pomegranate) Seed Oil
*Rubus Occidentalis* (Black Raspberry) Seed Oil
*Vaccinium Macrocarpon* (Cranberry) Seed Oil
*Citrullus Lanatus* (Watermelon) Seed Oil
*Rubus Idaeus* (Raspberry) Seed Oil
*Salvia Hispanica* (Chia) Seed Oil
Tetrahexadecyl Ascorbate
Ceteth-20
Steareth-20
Allantoin
Chlorphenesin
Hexapeptide-2
*Jojoba* Esters
*Moringa* Oil/Hydrogenated *Moringa* Oil Esters
Bisabolol
Fragrance
Sodium Bisulfite
Sodium Sulfite
Tocopheryl Acetate
Xanthan Gum
Citric Acid
Potassium Sorbate
Sodium Benzoate
Dextran
Sodium Hyaluronate
BHT
Stearyl Glycyrrhetinate
Disodium EDTA
Phenoxyethanol
Hydroxyethylcellulose
Glycyrrhiza *Glabra* (Licorice) Root Extract In certain embodiments, the invention relates to a formulation consisting essentially of
Purified Water
Hydrofluorocarbon 227ea
Pentylene Glycol
Cyclomethicone
Niacinamide
Isononyl Isononoate
C12-C15 Alkyl Ethylhexanoate
Glycerin
Hydroquinone
Alpha-Arbutin
Dimethicone/Divinyldimethicone/Silsesquioxane Crosspolymer
*Moringa Oleifera* Seed Oil Glyceryl Stearate
Cetyl Alcohol
Dimethicone
Cetearyl Alcohol
Kojic Acid
Panthenol
1-Methylhydantoine-2-Imide
Algae Extract and Mugwort (*Artemisia vulgaris*) Extract
Magnesium Aluminum Silicate
PEG-75 Stearate
*Avena Sativa* (Oat) Kernel Extract
*Saccharomyces/Xylinum*/Black Tea Ferment
*Palmaria Palmata* Extract
*Brassica Napus* Extract
*Punica Granatum* (Pomegranate) Seed Oil
*Rubus Occidentalis* (Black Raspberry) Seed Oil
*Vaccinium Macrocarpon* (Cranberry) Seed Oil
*Citrullus Lanatus* (Watermelon) Seed Oil
*Rubus Idaeus* (Raspberry) Seed Oil
*Salvia Hispanica* (Chia) Seed Oil
Tetrahexadecyl Ascorbate
Ceteth-20
Steareth-20
Allantoin
Chlorphenesin
Hexapeptide-2
*Jojoba* Esters
*Moringa* Oil/Hydrogenated *Moringa* Oil Esters
Bisabolol
Fragrance
Sodium Bisulfite
Sodium Sulfite
Tocopheryl Acetate
Xanthan Gum
Citric Acid
Potassium Sorbate
Sodium Benzoate
Dextran
Sodium Hyaluronate
BHT
Stearyl Glycyrrhetinate
Disodium EDTA
Phenoxyethanol
Hydroxyethylcellulose
*Glycyrrhiza Glabra* (Licorice) Root Extract In certain embodiments, the invention relates to a formulation consisting of
  Purified Water
  Hydrofluorocarbon 227ea
  Pentylene Glycol
  Cyclomethicone
  Niacinamide
  Isononyl Isononoate
  C12-C15 Alkyl Ethylhexanoate
  Glycerin
  Hydroquinone
  Alpha-Arbutin
  Dimethicone/Divinyldimethicone/Silsesquioxane Crosspolymer
  *Moringa Oleifera* Seed Oil
  Glyceryl Stearate
  Cetyl Alcohol
  Dimethicone
  Cetearyl Alcohol
  Kojic Acid
  Panthenol
  1-Methylhydantoine-2-Imide
  Algae Extract and Mugwort (*Artemisia vulgaris*) Extract
  Magnesium Aluminum Silicate
  PEG-75 Stearate
  *Avena Sativa* (Oat) Kernel Extract
  *Saccharomyces/Xylinum*/Black Tea Ferment
  *Palmaria Palmata* Extract
  *Brassica Napus* Extract
  *Punica Granatum* (Pomegranate) Seed Oil
  *Rubus Occidentalis* (Black Raspberry) Seed Oil
  *Vaccinium Macrocarpon* (Cranberry) Seed Oil
  *Citrullus Lanatus* (Watermelon) Seed Oil
  *Rubus Idaeus* (Raspberry) Seed Oil
  *Salvia Hispanica* (Chia) Seed Oil
  Tetrahexadecyl Ascorbate
  Ceteth-20
  Steareth-20
  Allantoin
  Chlorphenesin
  Hexapeptide-2
  *Jojoba* Esters
  *Moringa* Oil/Hydrogenated *Moringa* Oil Esters
  Bisabolol
  Fragrance
  Sodium Bisulfite
  Sodium Sulfite
  Tocopheryl Acetate
  Xanthan Gum
  Citric Acid
  Potassium Sorbate
  Sodium Benzoate
  Dextran
  Sodium Hyaluronate
  BHT
  Stearyl Glycyrrhetinate
  Disodium EDTA
  Phenoxyethanol
  Hydroxyethylcellulose
  *Glycyrrhiza Glabra* (Licorice) Root Extract In certain embodiments, the invention relates to a formulation comprising, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 3% to about 7% |
| Niacinamide | From about 2% to about 6% |
| Isononyl Isononoate | From about 1% to about 4% |
| C12-C15 Alkyl Ethylhexanoate | From about 1% to about 4% |
| Glycerin | From about 1% to about 3% |
| Hydroquinone | From about 1% to about 3% |
| Alpha-Arbutin | From about 1% to about 3% |
| Dimethicone/Divinyldimethicone/Silsesquioxane Crosspolymer | From about 1% to about 3% |
| *Moringa Oleifera* Seed Oil | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (*Artemisia vulgaris*) Extract | From about 0.5% to about 1.5% |
| Magnesium Aluminum Silicate | From about 0.5% to about 1.5% |
| PEG-75 Stearate | From about 0.5% to about 1.5% |
| *Avena Sativa* (Oat) Kernel Extract | From about 0.1% to about 1.0% |
| *Saccharomyces*/Xylinum/Black Tea Ferment | From about 0.2% to about 0.6% |
| *Palmaria Palmata* Extract | From about 0.1% to about 0.4% |
| *Brassica Napus* Extract | From about 0.3% to about 1.0% |

-continued

| | |
|---|---|
| Punica Granatum (Pomegranate) Seed Oil | From about 0.1% to about 0.4% |
| Rubus Occidentalis (Black Raspberry) Seed Oil | From about 0.1% to about 0.4% |
| Vaccinium Macrocarpon (Cranberry) Seed Oil | From about 0.1% to about 0.4% |
| Citrullus Lanatus (Watermelon) Seed Oil | From about 0.01% to about 0.05% |
| Rubus Idaeus (Raspberry) Seed Oil | From about 0.01% to about 0.05% |
| Salvia Hispanica (Chia) Seed Oil | From about 0.01% to about 0.05% |
| Tetrahexadecyl Ascorbate | From about 0.3% to about 0.7% |
| Ceteth-20 | From about 0.2% to about 0.6% |
| Steareth-20 | From about 0.2% to about 0.6% |
| Allantoin | From about 0.3% to about 0.7% |
| Chlorphenesin | From about 0.1% to about 0.4% |
| Hexapeptide-2 | From about 0.1% to about 1.0% |
| Jojoba Esters | From about 0.1% to about 0.4% |
| Moringa Oil/Hydrogenated Moringa Oil Esters | From about 0.1% to about 0.4% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.05% to about 0.15% |
| Xanthan Gum | From about 0.05% to about 0.15% |
| Citric Acid | From about 0.1% to about 0.3% |
| Potassium Sorbate | From about 0.1% to about 0.3% |
| Sodium Benzoate | From about 0.1% to about 0.3% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.01% to about 0.10% |
| Hydroxyethylcellulose | From about 0.1% to about 1.0% |
| Glycyrrhiza Glabra (Licorice) Root Extract | From about 0.02% to about 0.07% |

In certain embodiments, the invention relates to a formulation consisting essentially of, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 3% to about 7% |
| Niacinamide | From about 2% to about 6% |
| Isononyl Isononoate | From about 1% to about 4% |
| C12-C15 Alkyl Ethylhexanoate | From about 1% to about 4% |
| Glycerin | From about 1% to about 3% |
| Hydroquinone | From about 1% to about 3% |
| Alpha-Arbutin | From about 1% to about 3% |
| Dimethicone/Divinyldimethicone/ Silsesquioxane Crosspolymer | From about 1% to about 3% |
| Moringa Oleifera Seed Oil | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (Artemisia Vulgaris) Extract | From about 0.5% to about 1.5% |
| Magnesium Aluminum Silicate | From about 0.5% to about 1.5% |
| PEG-75 Stearate | From about 0.5% to about 1.5% |
| Avena Sativa (Oat) Kernel Extract | From about 0.1% to about 1.0% |
| Saccharomyces/Xylinum/ Black Tea Ferment | From about 0.2% to about 0.6% |
| Palmaria Palmata Extract | From about 0.1% to about 0.4% |
| Brassica Napus Extract | From about 0.3% to about 1.0% |
| Punica Granatum (Pomegranate) Seed Oil | From about 0.1% to about 0.4% |
| Rubus Occidentalis (Black Raspberry) Seed Oil | From about 0.1% to about 0.4% |
| Vaccinium Macrocarpon (Cranberry) Seed Oil | From about 0.1% to about 0.4% |
| Citrullus Lanatus (Watermelon) Seed Oil | From about 0.01% to about 0.05% |
| Rubus Idaeus (Raspberry) Seed Oil | From about 0.01% to about 0.05% |
| Salvia Hispanica (Chia) Seed Oil | From about 0.01% to about 0.05% |
| Tetrahexadecyl Ascorbate | From about 0.3% to about 0.7% |
| Ceteth-20 | From about 0.2% to about 0.6% |
| Steareth-20 | From about 0.2% to about 0.6% |
| Allantoin | From about 0.3% to about 0.7% |
| Chlorphenesin | From about 0.1% to about 0.4% |
| Hexapeptide-2 | From about 0.1% to about 1.0% |
| Jojoba Esters | From about 0.1% to about 0.4% |
| Moringa Oil/Hydrogenated Moringa Oil Esters | From about 0.1% to about 0.4% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.05% to about 0.15% |
| Xanthan Gum | From about 0.05% to about 0.15% |
| Citric Acid | From about 0.1% to about 0.3% |
| Potassium Sorbate | From about 0.1% to about 0.3% |
| Sodium Benzoate | From about 0.1% to about 0.3% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.01% to about 0.10% |
| Hydroxyethylcellulose | From about 0.1% to about 1.0% |
| Glycyrrhiza Glabra (Licorice) Root Extract | From about 0.02% to about 0.07% |

In certain embodiments, the invention relates to a formulation consisting of, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 3% to about 7% |
| Niacinamide | From about 2% to about 6% |
| Isononyl Isononoate | From about 1% to about 4% |
| C12-C15 Alkyl Ethylhexanoate | From about 1% to about 4% |
| Glycerin | From about 1% to about 3% |
| Hydroquinone | From about 1% to about 3% |
| Alpha-Arbutin | From about 1% to about 3% |
| Dimethicone/Divinyldimethicone/ Silsesquioxane Crosspolymer | From about 1% to about 3% |
| Moringa Oleifera Seed Oil | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (Artemisia vulgaris) Extract | From about 0.5% to about 1.5% |
| Magnesium Aluminum Silicate | From about 0.5% to about 1.5% |
| PEG-75 Stearate | From about 0.5% to about 1.5% |
| Avena Sativa (Oat) Kernel Extract | From about 0.1% to about 1.0% |
| Saccharomyces/Xylinum/Black Tea Ferment | From about 0.2% to about 0.6% |
| Palmaria Palmata Extract | From about 0.1% to about 0.4% |
| Brassica Napus Extract | From about 0.3% to about 1.0% |
| Punica Granatum (Pomegranate) Seed Oil | From about 0.1% to about 0.4% |
| Rubus Occidentalis (Black Raspberry) Seed Oil | From about 0.1% to about 0.4% |
| Vaccinium Macrocarpon (Cranberry) Seed Oil | From about 0.1% to about 0.4% |
| Citrullus Lanatus (Watermelon) Seed Oil | From about 0.01% to about 0.05% |
| Rubus Idaeus (Raspberry) Seed Oil | From about 0.01% to about 0.05% |
| Salvia Hispanica (Chia) Seed Oil | From about 0.01% to about 0.05% |
| Tetrahexadecyl Ascorbate | From about 0.3% to about 0.7% |

| | |
|---|---|
| Ceteth-20 | From about 0.2% to about 0.6% |
| Steareth-20 | From about 0.2% to about 0.6% |
| Allantoin | From about 0.3% to about 0.7% |
| Chlorphenesin | From about 0.1% to about 0.4% |
| Hexapeptide-2 | From about 0.1% to about 1.0% |
| Jojoba Esters | From about 0.1% to about 0.4% |
| *Moringa* Oil/Hydrogenated *Moringa* Oil Esters | From about 0.1% to about 0.4% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.05% to about 0.15% |
| Xanthan Gum | From about 0.05% to about 0.15% |
| Citric Acid | From about 0.1% to about 0.3% |
| Potassium Sorbate | From about 0.1% to about 0.3% |
| Sodium Benzoate | From about 0.1% to about 0.3% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.01% to about 0.10% |
| Hydroxyethylcellulose | From about 0.1% to about 1.0% |
| *Glycyrrhiza Glabra* (Licorice) Root Extract | From about 0.02% to about 0.07% |

In certain embodiments, the invention relates to a formulation comprising, by weight of the formulation

| | |
|---|---|
| Purified Water | About 53.165% |
| Hydrofluorocarbon 227ea | About 12.5% |
| Pentylene Glycol | About 5.3% |
| Cyclomethicone | About 5.0% |
| Niacinamide | About 4% |
| Isononyl Isononoate | About 2.5% |
| C12-C15 Alkyl Ethylhexanoate | About 2.5% |
| Glycerin | About 2.175% |
| Hydroquinone | About 2% |
| Alpha-Arbutin | About 2% |
| Dimethicone/Divinyldimethicone/ Silsesquioxane Crosspolymer | About 2% |
| *Moringa Oleifera* Seed Oil | About 2% |
| Glyceryl Stearate | About 1.69% |
| Cetyl Alcohol | About 1.69% |
| Dimethicone | About 1.25% |
| Cetearyl Alcohol | About 1% |
| Kojic Acid | About 1% |
| Panthenol | About 1% |
| 1-Methylhydantoine-2-Imide | About 1% |
| Algae Extract and Mugwort (*Artemisia vulgaris*) Extract | About 1% |
| Magnesium Aluminum Silicate | About 1% |
| PEG-75 Stearate | About 0.875% |
| *Avena Sativa* (Oat) Kernel Extract | < About 1% |
| *Saccharomyces/Xylinum*/Black Tea Ferment | About 0.44% |
| *Palmaria Palmata* Extract | About 0.3% |
| *Brassica Napus* Extract | About 0.075% |
| *Punica Granatum* (Pomegranate) Seed Oil | About 0.3% |
| *Rubus Occidentalis* (Black Raspberry) Seed Oil | About 0.3% |
| *Vaccinium Macrocarpon* (Cranberry) Seed Oil | About 0.3% |
| *Citrullus Lanatus* (Watermelon) Seed Oil | < About 0.05% |
| *Rubus Idaeus* (Raspberry) Seed Oil | < About 0.05% |
| *Salvia Hispanica* (Chia) Seed Oil | < About 0.05% |
| Tetrahexadecyl Ascorbate | About 0.5% |
| Ceteth-20 | About 0.37% |
| Steareth-20 | About 0.37% |
| Allantoin | About 0.49% |
| Chlorphenesin | About 0.3% |
| Hexapeptide-2 | < About 1% |
| Jojoba Esters | About 0.25% |
| *Moringa* Oil/Hydrogenated *Moringa* Oil Esters | About 0.25% |
| Bisabolol | About 0.2% |
| Fragrance | About 0.2% |
| Sodium Bisulfite | About 0.05% |
| Sodium Sulfite | About 0.05% |
| Tocopheryl Acetate | About 0.1% |
| Xanthan Gum | About 0.1% |
| Citric Acid | About 0.15% |
| Potassium Sorbate | About 0.15% |
| Sodium Benzoate | About 0.15% |
| Dextran | < About 1% |
| Sodium Hyaluronate | About 0.01% |
| BHT | About 0.2% |
| Stearyl Glycyrrhetinate | About 0.1% |
| Disodium EDTA | About 0.1% |
| Phenoxyethanol | < About 0.1% |
| Hydroxyethylcellulose | < About 1% |
| *Glycyrrhiza Glabra* (Licorice) Root Extract | About 0.05% |

In certain embodiments, the invention relates to a formulation consisting essentially of, by weight of the formulation

| | |
|---|---|
| Purified Water | About 53.165% |
| Hydrofluorocarbon 227ea | About 12.5% |
| Pentylene Glycol | About 5.3% |
| Cyclomethicone | About 5.0% |
| Niacinamide | About 4% |
| Isononyl Isononoate | About 2.5% |
| C12-C15 Alkyl Ethylhexanoate | About 2.5% |
| Glycerin | About 2.175% |
| Hydroquinone | About 2% |
| Alpha-Arbutin | About 2% |
| Dimethicone/Divinyldimethicone/ Silsesquioxane Crosspolymer | About 2% |
| *Moringa Oleifera* Seed Oil | About 2% |
| Glyceryl Stearate | About 1.69% |
| Cetyl Alcohol | About 1.69% |
| Dimethicone | About 1.25% |
| Cetearyl Alcohol | About 1% |
| Kojic Acid | About 1% |
| Panthenol | About 1% |
| 1-Methylhydantoine-2-Imide | About 1% |
| Algae Extract and Mugwort (*Artemisia vulgaris*) Extract | About 1% |
| Magnesium Aluminum Silicate | About 1% |
| PEG-75 Stearate | About 0.875% |
| *Avena Sativa* (Oat) Kernel Extract | < About 1% |
| *Saccharomyces/Xylinum*/Black Tea Ferment | About 0.44% |
| *Palmaria Palmata* Extract | About 0.3% |
| *Brassica Napus* Extract | About 0.075% |
| *Punica Granatum* (Pomegranate) Seed Oil | About 0.3% |
| *Rubus Occidentalis* (Black Raspberry) Seed Oil | About 0.3% |
| *Vaccinium Macrocarpon* (Cranberry) Seed Oil | About 0.3% |
| *Citrullus Lanatus* (Watermelon) Seed Oil | < About 0.05% |
| *Rubus Idaeus* (Raspberry) Seed Oil | < About 0.05% |
| *Salvia Hispanica* (Chia) Seed Oil | < About 0.05% |
| Tetrahexadecyl Ascorbate | About 0.5% |
| Ceteth-20 | About 0.37% |
| Steareth-20 | About 0.37% |
| Allantoin | About 0.49% |
| Chlorphenesin | About 0.3% |
| Hexapeptide-2 | < About 1% |
| Jojoba Esters | About 0.25% |
| *Moringa* Oil/Hydrogenated *Moringa* Oil Esters | About 0.25% |
| Bisabolol | About 0.2% |
| Fragrance | About 0.2% |
| Sodium Bisulfite | About 0.05% |
| Sodium Sulfite | About 0.05% |
| Tocopheryl Acetate | About 0.1% |

-continued

| | |
|---|---|
| Xanthan Gum | About 0.1% |
| Citric Acid | About 0.15% |
| Potassium Sorbate | About 0.15% |
| Sodium Benzoate | About 0.15% |
| Dextran | < About 1% |
| Sodium Hyaluronate | About 0.01% |
| BHT | About 0.2% |
| Stearyl Glycyrrhetinate | About 0.1% |
| Disodium EDTA | About 0.1% |
| Phenoxyethanol | < About 0.1% |
| Hydroxyethylcellulose | < About 1% |
| *Glycyrrhiza Glabra* (Licorice) Root Extract | About 0.05% |

In certain embodiments, the invention relates to a formulation consisting of, by weight of the formulation

| | |
|---|---|
| Purified Water | About 53.165% |
| Hydrofluorocarbon 227ea | About 12.5% |
| Pentylene Glycol | About 5.3% |
| Cyclomethicone | About 5.0% |
| Niacinamide | About 4% |
| Isononyl Isononoate | About 2.5% |
| C12-C15 Alkyl Ethylhexanoate | About 2.5% |
| Glycerin | About 2.175% |
| Hydroquinone | About 2% |
| Alpha-Arbutin | About 2% |
| Dimethicone/Divinyldimethicone/ Silsesquioxane Crosspolymer | About 2% |
| *Moringa Oleifera* Seed Oil | About 2% |
| Glyceryl Stearate | About 1.69% |
| Cetyl Alcohol | About 1.69% |
| Dimethicone | About 1.25% |
| Cetearyl Alcohol | About 1% |
| Kojic Acid | About 1% |
| Panthenol | About 1% |
| 1-Methylhydantoine-2-Imide | About 1% |
| Algae Extract and Mugwort (*Artemisia vulgaris*) Extract | About 1% |
| Magnesium Aluminum Silicate | About 1% |
| PEG-75 Stearate | About 0.875% |
| *Avena Sativa* (Oat) Kernel Extract | < About 1% |
| *Saccharomyces/Xylinum*/Black Tea Ferment | About 0.44% |
| *Palmaria Palmata* Extract | About 0.3% |
| *Brassica Napus* Extract | About 0.075% |
| *Punica Granatum* (Pomegranate) Seed Oil | About 0.3% |
| *Rubus Occidentalis* (Black Raspberry) Seed Oil | About 0.3% |
| *Vaccinium Macrocarpon* (Cranberry) Seed Oil | About 0.3% |
| *Citrullus Lanatus* (Watermelon) Seed Oil | < About 0.05% |
| *Rubus Idaeus* (Raspberry) Seed Oil | < About 0.05% |
| *Salvia Hispanica* (Chia) Seed Oil | < About 0.05% |
| Tetrahexadecyl Ascorbate | About 0.5% |
| Ceteth-20 | About 0.37% |
| Steareth-20 | About 0.37% |
| Allantoin | About 0.49% |
| Chlorphenesin | About 0.3% |
| Hexapeptide-2 | < About 1% |
| Jojoba Esters | About 0.25% |
| *Moringa* Oil/Hydrogenated *Moringa* Oil Esters | About 0.25% |
| Bisabolol | About 0.2% |
| Fragrance | About 0.2% |
| Sodium Bisulfite | About 0.05% |
| Sodium Sulfite | About 0.05% |
| Tocopheryl Acetate | About 0.1% |
| Xanthan Gum | About 0.1% |
| Citric Acid | About 0.15% |
| Potassium Sorbate | About 0.15% |
| Sodium Benzoate | About 0.15% |
| Dextran | < About 1% |
| Sodium Hyaluronate | About 0.01% |
| BHT | About 0.2% |

-continued

| | |
|---|---|
| Stearyl Glycyrrhetinate | About 0.1% |
| Disodium EDTA | About 0.1% |
| Phenoxyethanol | < About 0.1% |
| Hydroxyethylcellulose | < About 1% |
| *Glycyrrhiza Glabra* (Licorice) Root Extract | About 0.05% |

In certain embodiments, the invention relates to a formulation comprising
  Purified Water
  Hydrofluorocarbon 227ea
  Pentylene Glycol
  Cyclomethicone
  Niacinamide
  Isononyl Isononoate
  C12-C15 Alkyl Ethylhexanoate
  Glycerin
  Hydroquinone
  Alpha-Arbutin
  Dimethicone/Divinyldimethicone/Silsesquioxane Crosspolymer
  Glyceryl Stearate
  Cetyl Alcohol
  Dimethicone
  Cetearyl Alcohol
  Kojic Acid
  Panthenol
  1-Methylhydantoine-2-Imide
  Algae Extract and Mugwort (*Artemisia vulgaris*) Extract
  Magnesium Aluminum Silicate
  PEG-75 Stearate
  *Avena Sativa* (Oat) Kernel Extract
  *Saccharomyces/Xylinum*/Black Tea Ferment
  *Palmaria Palmata* Extract
  *Brassica Napus* Extract
  *Punica Granatum* (Pomegranate) Seed Oil
  *Rubus Occidentalis* (Black Raspberry) Seed Oil
  *Vaccinium Macrocarpon* (Cranberry) Seed Oil
  *Citrullus Lanatus* (Watermelon) Seed Oil
  *Rubus Idaeus* (Raspberry) Seed Oil
  *Salvia Hispanica* (Chia) Seed Oil
  Tetrahexadecyl Ascorbate
  Ceteth-20
  Steareth-20
  Allantoin
  Chlorphenesin
  Hexapeptide-2
  Bisabolol
  Fragrance
  Sodium Bisulfite
  Sodium Sulfite
  Tocopheryl Acetate
  Xanthan Gum
  Citric Acid
  Potassium Sorbate
  Sodium Benzoate
  Dextran
  Sodium Hyaluronate
  BHT
  Stearyl Glycyrrhetinate
  Disodium EDTA
  Phenoxyethanol
  Hydroxyethylcellulose
  *Glycyrrhiza Glabra* (Licorice) Root Extract Acacia Decurrens/*Jojoba*/Sunflower Seed Wax Polyglyceryl-3 Esters
*Butyrospermum Parkii* (Shea) Butter In certain embodiments, the invention relates to a formulation consisting essentially of
Purified Water
Hydrofluorocarbon 227ea
Pentylene Glycol
Cyclomethicone
Niacinamide
Isononyl Isononoate
C12-C15 Alkyl Ethylhexanoate
Glycerin
Hydroquinone
Alpha-Arbutin
Dimethicone/Divinyldimethicone/Silsesquioxane Crosspolymer
Glyceryl Stearate
Cetyl Alcohol
Dimethicone
Cetearyl Alcohol
Kojic Acid
Panthenol
1-Methylhydantoine-2-Imide
Algae Extract and Mugwort (*Artemisia vulgaris*) Extract
Magnesium Aluminum Silicate
PEG-75 Stearate
*Avena Sativa* (Oat) Kernel Extract
*Saccharomyces/Xylinum*/Black Tea Ferment
*Palmaria Palmata* Extract
*Brassica Napus* Extract
*Punica Granatum* (Pomegranate) Seed Oil
*Rubus Occidentalis* (Black Raspberry) Seed Oil
*Vaccinium Macrocarpon* (Cranberry) Seed Oil
*Citrullus Lanatus* (Watermelon) Seed Oil
*Rubus Idaeus* (Raspberry) Seed Oil
*Salvia Hispanica* (Chia) Seed Oil
Tetrahexadecyl Ascorbate
Ceteth-20
Steareth-20
Allantoin
Chlorphenesin
Hexapeptide-2
Bisabolol
Fragrance
Sodium Bisulfite
Sodium Sulfite
Tocopheryl Acetate
Xanthan Gum
Citric Acid
Potassium Sorbate
Sodium Benzoate
Dextran
Sodium Hyaluronate
BHT
Stearyl Glycyrrhetinate
Disodium EDTA
Phenoxyethanol
Hydroxyethylcellulose
*Glycyrrhiza Glabra* (Licorice) Root Extract
Acacia Decurrens/*Jojoba*/Sunflower Seed Wax Polyglyceryl-3 Esters
*Butyrospermum Parkii* (Shea) Butter In certain embodiments, the invention relates to a formulation consisting of
Purified Water
Hydrofluorocarbon 227ea
Pentylene Glycol
Cyclomethicone
Niacinamide
Isononyl Isononoate
C12-C15 Alkyl Ethylhexanoate
Glycerin
Hydroquinone
Alpha-Arbutin
Dimethicone/Divinyldimethicone/Silsesquioxane Crosspolymer
Glyceryl Stearate
Cetyl Alcohol
Dimethicone
Cetearyl Alcohol
Kojic Acid
Panthenol
1-Methylhydantoine-2-Imide
Algae Extract and Mugwort (*Artemisia vulgaris*) Extract
Magnesium Aluminum Silicate
PEG-75 Stearate
*Avena Sativa* (Oat) Kernel Extract
*Saccharomyces/Xylinum*/Black Tea Ferment
*Palmaria Palmata* Extract
*Brassica Napus* Extract
*Punica Granatum* (Pomegranate) Seed Oil
*Rubus Occidentalis* (Black Raspberry) Seed Oil
*Vaccinium Macrocarpon* (Cranberry) Seed Oil
*Citrullus Lanatus* (Watermelon) Seed Oil
*Rubus Idaeus* (Raspberry) Seed Oil
*Salvia Hispanica* (Chia) Seed Oil
Tetrahexadecyl Ascorbate
Ceteth-20
Steareth-20
Allantoin
Chlorphenesin
Hexapeptide-2
Bisabolol
Fragrance
Sodium Bisulfite
Sodium Sulfite
Tocopheryl Acetate
Xanthan Gum
Citric Acid
Potassium Sorbate
Sodium Benzoate
Dextran
Sodium Hyaluronate
BHT
Stearyl Glycyrrhetinate
Disodium EDTA
Phenoxyethanol
Hydroxyethylcellulose
*Glycyrrhiza Glabra* (Licorice) Root Extract
Acacia Decurrens/*Jojoba*/Sunflower Seed Wax Polyglyceryl-3 Esters
*Butyrospermum Parkii* (Shea) Butter In certain embodiments, the invention relates to a formulation comprising, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 1% to about 2% |
| Niacinamide | From about 2% to about 6% |
| Isononyl Isononoate | From about 1% to about 3% |
| C12-C15 Alkyl Ethylhexanoate | From about 1% to about 3% |

-continued

| | |
|---|---|
| Glycerin | From about 1% to about 3% |
| Hydroquinone | From about 1% to about 3% |
| Alpha-Arbutin | From about 1% to about 3% |
| Dimethicone/Divinyldimethicone/Silsesquioxane Crosspolymer | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (*Artemisia vulgaris*) Extract | From about 0.5% to about 1.5% |
| Magnesium Aluminum Silicate | From about 0.5% to about 1.5% |
| PEG-75 Stearate | From about 0.5% to about 1.5% |
| *Avena Sativa* (Oat) Kernel Extract | From about 0.1% to about 1.0% |
| *Saccharomyces/Xylinum*/Black Tea Ferment | From about 1% to about 4% |
| *Palmaria Palmata* Extract | From about 0.1% to about 0.5% |
| *Brassica Napus* Extract | From about 0.04% to about 0.1% |
| *Punica Granatum* (Pomegranate) Seed Oil | From about 0.3% to about 0.9% |
| *Rubus Occidentalis* (Black Raspberry) Seed Oil | From about 0.3% to about 0.9% |
| *Vaccinium Macrocarpon* (Cranberry) Seed Oil | From about 0.3% to about 0.9% |
| *Citrullus Lanatus* (Watermelon) Seed Oil | From about 0.06% to about 0.13% |
| *Rubus Idaeus* (Raspberry) Seed Oil | From about 0.06% to about 0.13% |
| *Salvia Hispanica* (Chia) Seed Oil | From about 0.06% to about 0.13% |
| Tetrahexadecyl Ascorbate | From about 0.2% to about 0.7% |
| Ceteth-20 | From about 0.1% to about 0.5% |
| Steareth-20 | From about 0.1% to about 0.5% |
| Allantoin | From about 0.2% to about 0.7% |
| Chlorphenesin | From about 0.1% to about 0.5% |
| Hexapeptide-2 | From about 0.1% to about 1.0% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.2% to about 0.7% |
| Xanthan Gum | From about 0.05% to about 0.15% |
| Citric Acid | From about 0.05% to about 0.20% |
| Potassium Sorbate | From about 0.05% to about 0.20% |
| Sodium Benzoate | From about 0.05% to about 0.20% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.05% to about 0.1% |
| Hydroxyethylcellulose | From about 0.1% to about 1.0% |
| *Glycyrrhiza Glabra* (Licorice) Root Extract | From about 0.02% to about 0.07% |
| *Acacia Decurrens*/Jojoba/Sunflower Seed Wax Polyglyceryl-3 Esters | From about 1% to about 3% |
| *Butyrospermum Parkii* (Shea) Butter | From about 1% to about 3% |

In certain embodiments, the invention relates to a formulation consisting essentially of, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 1% to about 2% |
| Niacinamide | From about 2% to about 6% |
| Isononyl Isononoate | From about 1% to about 3% |
| C12-C15 Alkyl Ethylhexanoate | From about 1% to about 3% |
| Glycerin | From about 1% to about 3% |
| Hydroquinone | From about 1% to about 3% |
| Alpha-Arbutin | From about 1% to about 3% |
| Dimethicone/Divinyldimethicone/Silsesquioxane Crosspolymer | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (*Artemisia vulgaris*) Extract | From about 0.5% to about 1.5% |
| Magnesium Aluminum Silicate | From about 0.5% to about 1.5% |
| PEG-75 Stearate | From about 0.5% to about 1.5% |
| *Avena Sativa* (Oat) Kernel Extract | From about 0.1% to about 1.0% |
| *Saccharomyces/Xylinum*/Black Tea Ferment | From about 1% to about 4% |
| *Palmaria Palmata* Extract | From about 0.1% to about 0.5% |
| *Brassica Napus* Extract | From about 0.04% to about 0.1% |
| *Punica Granatum* (Pomegranate) Seed Oil | From about 0.3% to about 0.9% |
| *Rubus Occidentalis* (Black Raspberry) Seed Oil | From about 0.3% to about 0.9% |
| *Vaccinium Macrocarpon* (Cranberry) Seed Oil | From about 0.3% to about 0.9% |
| *Citrullus Lanatus* (Watermelon) Seed Oil | From about 0.06% to about 0.13% |
| *Rubus Idaeus* (Raspberry) Seed Oil | From about 0.06% to about 0.13% |
| *Salvia Hispanica* (Chia) Seed Oil | From about 0.06% to about 0.13% |
| Tetrahexadecyl Ascorbate | From about 0.2% to about 0.7% |
| Ceteth-20 | From about 0.1% to about 0.5% |
| Steareth-20 | From about 0.1% to about 0.5% |
| Allantoin | From about 0.2% to about 0.7% |
| Chlorphenesin | From about 0.1% to about 0.5% |
| Hexapeptide-2 | From about 0.1% to about 1.0% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.2% to about 0.7% |
| Xanthan Gum | From about 0.05% to about 0.15% |
| Citric Acid | From about 0.05% to about 0.20% |
| Potassium Sorbate | From about 0.05% to about 0.20% |
| Sodium Benzoate | From about 0.05% to about 0.20% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.05% to about 0.1% |
| Hydroxyethylcellulose | From about 0.1% to about 1.0% |
| *Glycyrrhiza Glabra* (Licorice) Root Extract | From about 0.02% to about 0.07% |
| *Acacia Decurrens*/Jojoba/Sunflower Seed Wax Polyglyceryl-3 Esters | From about 1% to about 3% |
| *Butyrospermum Parkii* (Shea) Butter | From about 1% to about 3% |

In certain embodiments, the invention relates to a formulation consisting of, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 1% to about 2% |
| Niacinamide | From about 2% to about 6% |
| Isononyl Isononoate | From about 1% to about 3% |
| C12-C15 Alkyl Ethylhexanoate | From about 1% to about 3% |
| Glycerin | From about 1% to about 3% |
| Hydroquinone | From about 1% to about 3% |
| Alpha-Arbutin | From about 1% to about 3% |
| Dimethicone/Divinyldimethicone/Silsesquioxane Crosspolymer | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |

-continued

| | |
|---|---|
| Algae Extract and Mugwort (*Artemisia vulgaris*) Extract | From about 0.5% to about 1.5% |
| Magnesium Aluminum Silicate | From about 0.5% to about 1.5% |
| PEG-75 Stearate | From about 0.5% to about 1.5% |
| *Avena Sativa* (Oat) Kernel Extract | From about 0.1% to about 1.0% |
| *Saccharomyces/Xylinum*/Black Tea Ferment | From about 1% to about 4% |
| *Palmaria Palmata* Extract | From about 0.1% to about 0.5% |
| *Brassica Napus* Extract | From about 0.04% to about 0.1% |
| *Punica Granatum* (Pomegranate) Seed Oil | From about 0.3% to about 0.9% |
| *Rubus Occidentalis* (Black Raspberry) Seed Oil | From about 0.3% to about 0.9% |
| *Vaccinium Macrocarpon* (Cranberry) Seed Oil | From about 0.3% to about 0.9% |
| *Citrullus Lanatus* (Watermelon) Seed Oil | From about 0.06% to about 0.13% |
| *Rubus Idaeus* (Raspberry) Seed Oil | From about 0.06% to about 0.13% |
| *Salvia Hispanica* (Chia) Seed Oil | From about 0.06% to about 0.13% |
| Tetrahexadecyl Ascorbate | From about 0.2% to about 0.7% |
| Ceteth-20 | From about 0.1% to about 0.5% |
| Steareth-20 | From about 0.1% to about 0.5% |
| Allantoin | From about 0.2% to about 0.7% |
| Chlorphenesin | From about 0.1% to about 0.5% |
| Hexapeptide-2 | From about 0.1% to about 1.0% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.2% to about 0.7% |
| Xanthan Gum | From about 0.05% to about 0.15% |
| Citric Acid | From about 0.05% to about 0.20% |
| Potassium Sorbate | From about 0.05% to about 0.20% |
| Sodium Benzoate | From about 0.05% to about 0.20% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.05% to about 0.1% |
| Hydroxyethylcellulose | From about 0.1% to about 1.0% |
| *Glycyrrhiza Glabra* (Licorice) Root Extract | From about 0.02% to about 0.07% |
| *Acacia Decurrens*/Jojoba/ Sunflower Seed Wax Polyglyceryl-3 Esters | From about 1% to about 3% |
| *Butyrospermum Parkii* (Shea) Butter | From about 1% to about 3% |

In certain embodiments, the invention relates to a formulation comprising, by weight of the formulation

| | |
|---|---|
| Purified Water | About 53.08% |
| Hydrofluorocarbon 227ea | About 12.5% |
| Pentylene Glycol | About 5.3% |
| Cyclomethicone | About 1.5% |
| Niacinamide | About 4% |
| Isononyl Isononoate | About 2% |
| C12-C15 Alkyl Ethylhexanoate | About 2% |
| Glycerin | About 2.175% |
| Hydroquinone | About 2% |
| Alpha-Arbutin | About 2% |
| Dimethicone/Divinyldimethicone/ Silsesquioxane Crosspolymer | About 1.75% |
| Glyceryl Stearate | About 1.69% |
| Cetyl Alcohol | About 1.69% |
| Dimethicone | About 1% |
| Cetearyl Alcohol | About 1% |
| Kojic Acid | About 1% |
| Panthenol | About 1% |
| 1-Methylhydantoine-2-Imide | About 1% |
| Algae Extract and Mugwort (*Artemisia vulgaris*) Extract | About 1% |
| Magnesium Aluminum Silicate | About 1% |
| PEG-75 Stearate | About 0.875% |
| *Avena Sativa* (Oat) Kernel Extract | < About 1% |
| *Saccharomyces/Xylinum*/Black Tea Ferment | About 2.65% |
| *Palmaria Palmata* Extract | About 0.3% |
| *Brassica Napus* Extract | About 0.075% |
| *Punica Granatum* (Pomegranate) Seed Oil | About 0.625% |
| *Rubus Occidentalis* (Black Raspberry) Seed Oil | About 0.625% |
| *Vaccinium Macrocarpon* (Cranberry) Seed Oil | About 0.625% |
| *Citrullus Lanatus* (Watermelon) Seed Oil | < About 0.125% |
| *Rubus Idaeus* (Raspberry) Seed Oil | < About 0.125% |
| *Salvia Hispanica* (Chia) Seed Oil | < About 0.125% |
| Tetrahexadecyl Ascorbate | About 0.5% |
| Ceteth-20 | About 0.37% |
| Steareth-20 | About 0.37% |
| Allantoin | About 0.49% |
| Chlorphenesin | About 0.3% |
| Hexapeptide-2 | < About 1% |
| Bisabolol | About 0.2% |
| Fragrance | About 0.2% |
| Sodium Bisulfite | About 0.05% |
| Sodium Sulfite | About 0.05% |
| Tocopheryl Acetate | About 0.5% |
| Xanthan Gum | About 0.1% |
| Citric Acid | About 0.15% |
| Potassium Sorbate | About 0.15% |
| Sodium Benzoate | About 0.15% |
| Dextran | < About 1% |
| Sodium Hyaluronate | About 0.01% |
| BHT | About 0.2% |
| Stearyl Glycyrrhetinate | About 0.1% |
| Disodium EDTA | About 0.1% |
| Phenoxyethanol | < About 0.1% |
| Hydroxyethylcellulose | < About 1% |
| *Glycyrrhiza Glabra* (Licorice) Root Extract | About 0.05% |
| *Acacia Decurrens*/Jojoba/ Sunflower Seed Wax Polyglyceryl-3 Esters | About 2% |
| *Butyrospermum Parkii* (Shea) Butter | About 2% |

In certain embodiments, the invention relates to a formulation consisting essentially of, by weight of the formulation

| | |
|---|---|
| Purified Water | About 53.08% |
| Hydrofluorocarbon 227ea | About 12.5% |
| Pentylene Glycol | About 5.3% |
| Cyclomethicone | About 1.5% |
| Niacinamide | About 4% |
| Isononyl Isononoate | About 2% |
| C12-C15 Alkyl Ethylhexanoate | About 2% |
| Glycerin | About 2.175% |
| Hydroquinone | About 2% |
| Alpha-Arbutin | About 2% |
| Dimethicone/Divinyldimethicone/ Silsesquioxane Crosspolymer | About 1.75% |
| Glyceryl Stearate | About 1.69% |
| Cetyl Alcohol | About 1.69% |
| Dimethicone | About 1% |
| Cetearyl Alcohol | About 1% |
| Kojic Acid | About 1% |
| Panthenol | About 1% |
| 1-Methylhydantoine-2-Imide | About 1% |
| Algae Extract and Mugwort (*Artemisia vulgaris*) Extract | About 1% |
| Magnesium Aluminum Silicate | About 1% |
| PEG-75 Stearate | About 0.875% |
| *Avena Sativa* (Oat) Kernel Extract | < About 1% |
| *Saccharomyces/Xylinum*/Black Tea Ferment | About 2.65% |
| *Palmaria Palmata* Extract | About 0.3% |
| *Brassica Napus* Extract | About 0.075% |
| *Punica Granatum* (Pomegranate) Seed Oil | About 0.625% |

-continued

| | |
|---|---|
| Rubus Occidentalis (Black Raspberry) Seed Oil | About 0.625% |
| Vaccinium Macrocarpon (Cranberry) Seed Oil | About 0.625% |
| Citrullus Lanatus (Watermelon) Seed Oil | < About 0.125% |
| Rubus Idaeus (Raspberry) Seed Oil | < About 0.125% |
| Salvia Hispanica (Chia) Seed Oil | < About 0.125% |
| Tetrahexadecyl Ascorbate | About 0.5% |
| Ceteth-20 | About 0.37% |
| Steareth-20 | About 0.37% |
| Allantoin | About 0.49% |
| Chlorphenesin | About 0.3% |
| Hexapeptide-2 | < About 1% |
| Bisabolol | About 0.2% |
| Fragrance | About 0.2% |
| Sodium Bisulfite | About 0.05% |
| Sodium Sulfite | About 0.05% |
| Tocopheryl Acetate | About 0.5% |
| Xanthan Gum | About 0.1% |
| Citric Acid | About 0.15% |
| Potassium Sorbate | About 0.15% |
| Sodium Benzoate | About 0.15% |
| Dextran | < About 1% |
| Sodium Hyaluronate | About 0.01% |
| BHT | About 0.2% |
| Stearyl Glycyrrhetinate | About 0.1% |
| Disodium EDTA | About 0.1% |
| Phenoxyethanol | < About 0.1% |
| Hydroxyethylcellulose | < About 1% |
| Glycyrrhiza Glabra (Licorice) Root Extract | About 0.05% |
| Acacia Decurrens/Jojoba/Sunflower Seed Wax Polyglyceryl-3 Esters | About 2% |
| Butyrospermum Parkii (Shea) Butter | About 2% |

In certain embodiments, the invention relates to a formulation consisting of, by weight of the formulation

| | |
|---|---|
| Purified Water | About 53.08% |
| Hydrofluorocarbon 227ea | About 12.5% |
| Pentylene Glycol | About 5.3% |
| Cyclomethicone | About 1.5% |
| Niacinamide | About 4% |
| Isononyl Isononoate | About 2% |
| C12-C15 Alkyl Ethylhexanoate | About 2% |
| Glycerin | About 2.175% |
| Hydroquinone | About 2% |
| Alpha-Arbutin | About 2% |
| Dimethicone/Divinyldimethicone/Silsesquioxane Crosspolymer | About 1.75% |
| Glyceryl Stearate | About 1.69% |
| Cetyl Alcohol | About 1.69% |
| Dimethicone | About 1% |
| Cetearyl Alcohol | About 1% |
| Kojic Acid | About 1% |
| Panthenol | About 1% |
| 1-Methylhydantoine-2-Imide | About 1% |
| Algae Extract and Mugwort (Artemisia vulgaris) Extract | About 1% |
| Magnesium Aluminum Silicate | About 1% |
| PEG-75 Stearate | About 0.875% |
| Avena Sativa (Oat) Kernel Extract | < About 1% |
| Saccharomyces/Xylinum/Black Tea Ferment | About 2.65% |
| Palmaria Palmata Extract | About 0.3% |
| Brassica Napus Extract | About 0.075% |
| Punica Granatum (Pomegranate) Seed Oil | About 0.625% |
| Rubus Occidentalis (Black Raspberry) Seed Oil | About 0.625% |
| Vaccinium Macrocarpon (Cranberry) Seed Oil | About 0.625% |
| Citrullus Lanatus (Watermelon) Seed Oil | < About 0.125% |
| Rubus Idaeus (Raspberry) Seed Oil | < About 0.125% |
| Salvia Hispanica (Chia) Seed Oil | < About 0.125% |
| Tetrahexadecyl Ascorbate | About 0.5% |
| Ceteth-20 | About 0.37% |
| Steareth-20 | About 0.37% |
| Allantoin | About 0.49% |
| Chlorphenesin | About 0.3% |
| Hexapeptide-2 | < About 1% |
| Bisabolol | About 0.2% |
| Fragrance | About 0.2% |
| Sodium Bisulfite | About 0.05% |
| Sodium Sulfite | About 0.05% |
| Tocopheryl Acetate | About 0.5% |
| Xanthan Gum | About 0.1% |
| Citric Acid | About 0.15% |
| Potassium Sorbate | About 0.15% |
| Sodium Benzoate | About 0.15% |
| Dextran | < About 1% |
| Sodium Hyaluronate | About 0.01% |
| BHT | About 0.2% |
| Stearyl Glycyrrhetinate | About 0.1% |
| Disodium EDTA | About 0.1% |
| Phenoxyethanol | < About 0.1% |
| Hydroxyethylcellulose | < About 1% |
| Glycyrrhiza Glabra (Licorice) Root Extract | About 0.05% |
| Acacia Decurrens/Jojoba/Sunflower Seed Wax Polyglyceryl-3 Esters | About 2% |
| Butyrospermum Parkii (Shea) Butter | About 2% |

Exemplary Methods of Formulation

In certain embodiments, the invention relates to a method for increasing the efficacy of a hydroquinone-containing formulation comprising the step of adding an activating agent to the continuous phase of the formulation, wherein the formulation comprises an oil-in-water emulsion, thereby forming an improved hydroquinone-containing formulation.

In certain embodiments, the invention relates to any one of the aforementioned methods, wherein the improved hydroquinone-containing formulation is intended for topical administration.

In certain embodiments, the invention relates to any one of the aforementioned methods, wherein the improved hydroquinone-containing formulation is any one of the aforementioned formulations.

In certain embodiments, the invention relates to any one of the aforementioned methods, wherein a plurality of activating agents are added to the continuous phase.

In certain embodiments, the invention relates to a method for decreasing the irritancy of a hydroquinone-containing formulation comprising the step of adding an emollient and an anti-irritant to the formulation, wherein the formulation comprises an oil-in-water emulsion, thereby forming a less irritating hydroquinone-containing formulation.

In certain embodiments, the invention relates to any one of the aforementioned methods, wherein the less irritating hydroquinone-containing formulation is intended for topical administration.

In certain embodiments, the invention relates to any one of the aforementioned methods, wherein the less irritating hydroquinone-containing formulation is any one of the aforementioned formulations.

In certain embodiments, the invention relates to any one of the aforementioned methods, wherein the continuous phase comprises a plurality of activating agents.

In certain embodiments, the invention relates to any one of the aforementioned methods, wherein a plurality of emollients are added.

In certain embodiments, the invention relates to any one of the aforementioned methods, wherein a plurality of anti-irritants are added.

In certain embodiments, the invention relates to a method comprising the steps of:

combining, in a first container, BHT, stearyl glycyrrhetinate, cetyl alcohol, ceteth-20, steareth-20, glyceryl stearate, PEG-75 stearate, cetostearyl alcohol, *jojoba* esters, isonoyl isononanoate, $C_{12}$-$C_{15}$ alkyl ethylhexanoate, *moringa* butter, *moringa* oil, tocopheryl acetate, tetrahexadecyl ascorbate, bisabolol, dimethicone, dimethicone/divinyldimethicone/silsesquioxane crosspolymer, black raspberry seed oil, cranberry seed oil, pomegranate seed oil, watermelon seed oil, raspberry seed oil, and chia seed oil, thereby forming mixture A;

in a second container, adding, while homogenizing, magnesium aluminum silicate to water, thereby forming mixture B;

homogenizing mixture B:

in a third container, combining pentylene glycol and xanthan gum, thereby forming mixture C;

adding, in the second container, mixture C to mixture B, thereby forming mixture BC;

adding to mixture BC in the second container allantoin, sodium hyaluronate, panthenol, potassium sorbate, sodium benzoate, disodium EDTA, citric acid, and niacinamide, thereby forming mixture BCD.

adding to mixture BCD mixture A, thereby forming mixture ABCD;

adding to mixture ABCD algae extract, mugwort (*Artemisia vulgaris*) extract, water, glycerin, and *avena sativa* (Oat) kernel extract, thereby forming mixture E;

dissolving sodium bisulfite and sodium sulfite in water, thereby forming solution F;

adding solution F to mixture E, thereby forming mixture EF;

combining pentylene glycol and chlorphenesin, thereby forming mixture G;

adding mixture G to mixture EF, thereby forming mixture EFG;

adding to mixture EFG water, dextran, and hexapeptide-2, thereby forming mixture H;

combining water, pentylene glycol, and alpha-arbutin, thereby forming mixture I;

adding mixture I to mixture H, thereby forming mixture HI;

combining water, pentylene glycol, and kojic acid, thereby forming mixture J;

adding mixture J to mixture HI, thereby forming mixture HIJ;

adding to mixture HIJ cyclomethicone, water, glycerin, *brassica napus* extract, *palmaria palmata* extract, *saccharomyces/xylinum*/black tea ferment, and 1-methylhydantoine-2-imide, thereby forming mixture K;

combining pentylene glycol and licorice root extract, thereby forming mixture L;

adding mixture L to mixture K, thereby forming mixture KL;

combining pentylene glycol, water and hydroquinone, thereby forming mixture M; and adding mixture M to mixture KL, thereby forming a hydroquinone-containing formulation.

In certain embodiments, the invention relates to any one of the aforementioned methods, further comprising the step of heating mixture A to a temperature of about 75° C. In certain embodiments, the invention relates to any one of the aforementioned methods, further comprising the step of mixing mixture A.

In certain embodiments, the invention relates to any one of the aforementioned methods, wherein mixture B is homogenized for a period of about 5 min.

In certain embodiments, the invention relates to any one of the aforementioned methods, further comprising the step of mixing mixture C.

In certain embodiments, the invention relates to any one of the aforementioned methods, further comprising the step of mixing mixture BC. In certain embodiments, the invention relates to any one of the aforementioned methods, further comprising the step of mixing mixture BC for a period of about 15 min. In certain embodiments, the invention relates to any one of the aforementioned methods, further comprising the step of mixing mixture BC using a lightning mixer.

In certain embodiments, the invention relates to any one of the aforementioned methods, further comprising the step of heating mixture BCD to about 75° C.

In certain embodiments, the invention relates to any one of the aforementioned methods, further comprising the step of mixing mixture BCD.

In certain embodiments, the invention relates to any one of the aforementioned methods, wherein mixture A is at about 75° C. when it is added to mixture BCD.

In certain embodiments, the invention relates to any one of the aforementioned methods, further comprising the step of continuously mixing mixture A into mixture BCD.

In certain embodiments, the invention relates to any one of the aforementioned methods, further comprising the step of homogenizing mixture ABCD. In certain embodiments, the invention relates to any one of the aforementioned methods, further comprising the step of homogenizing mixture ABCD for a period of about 3 min.

In certain embodiments, the invention relates to any one of the aforementioned methods, further comprising the step of cooling mixture ABCD to about 35° C. In certain embodiments, the invention relates to any one of the aforementioned methods, further comprising the step of cooling mixture ABCD to about 35° C. without a water bath.

In certain embodiments, the invention relates to any one of the aforementioned methods, wherein algae extract, mugwort (*Artemisia vulgaris*) extract, water, glycerin, and *avena sativa* (Oat) kernel extract are added individually to mixture ABCD. In certain embodiments, the invention relates to any one of the aforementioned methods, wherein mixture ABCD is at about 35° C. when algae extract, mugwort (*Artemisia vulgaris*) extract, water, glycerin, or *avena sativa* (Oat) kernel extract is added.

In certain embodiments, the invention relates to any one of the aforementioned methods, further comprising the step of mixing mixture E.

In certain embodiments, the invention relates to any one of the aforementioned methods, wherein solution F is formed at about 22° C.

In certain embodiments, the invention relates to any one of the aforementioned methods, wherein mixture E is at about 35° C. when solution F is added.

In certain embodiments, the invention relates to any one of the aforementioned methods, further comprising the step of mixing mixture EF.

In certain embodiments, the invention relates to any one of the aforementioned methods, further comprising the step of heating mixture G. In certain embodiments, the invention relates to any one of the aforementioned methods, further comprising the step of heating mixture G to about 50° C.

In certain embodiments, the invention relates to any one of the aforementioned methods, further comprising the step of mixing mixture G.

In certain embodiments, the invention relates to any one of the aforementioned methods, further comprising the step of dissolving the chlorphenesin in mixture G.

In certain embodiments, the invention relates to any one of the aforementioned methods, wherein mixture EF is at about 35° C. when mixture G is added.

In certain embodiments, the invention relates to any one of the aforementioned methods, wherein mixture EFG is at about 35° C. when water, dextran, or hexapeptide-2 is added.

In certain embodiments, the invention relates to any one of the aforementioned methods, further comprising the step of mixing mixture H.

In certain embodiments, the invention relates to any one of the aforementioned methods, further comprising the step of cooling mixture H to about 32° C.

In certain embodiments, the invention relates to any one of the aforementioned methods, further comprising the step of mixing mixture I.

In certain embodiments, the invention relates to any one of the aforementioned methods, wherein mixture H is at about 30° C. to about 32° C. when mixture I is added.

In certain embodiments, the invention relates to any one of the aforementioned methods, further comprising the step of mixing mixture J until the kojic acid is suspended.

In certain embodiments, the invention relates to any one of the aforementioned methods, wherein mixture HI is at about 30° C. to about 32° C. when mixture J is added.

In certain embodiments, the invention relates to any one of the aforementioned methods, wherein cyclomethicone, water, glycerin, *brassica napus* extract, *palmaria palmata* extract, *saccharomyces/xylinum*/black tea ferment, and 1-methylhydantoine-2-imide are individually added to mixture HIJ.

In certain embodiments, the invention relates to any one of the aforementioned methods, wherein mixture HIJ is at about 30° C. when cyclomethicone, water, glycerin, *brassica napus* extract, *palmaria palmata* extract, *saccharomyces/xylinum*/black tea ferment, or 1-methylhydantoine-2-imide is added.

In certain embodiments, the invention relates to any one of the aforementioned methods, further comprising the step of mixing mixture L.

In certain embodiments, the invention relates to any one of the aforementioned methods, wherein mixture K is at about 30° C. when mixture L is added.

In certain embodiments, the invention relates to any one of the aforementioned methods, further comprising the step of mixing mixture M until all of the hydroquinone is dispersed.

In certain embodiments, the invention relates to any one of the aforementioned methods, wherein mixture KL is at about 30° C. when mixture M is added.

In certain embodiments, the invention relates to any one of the aforementioned methods, further comprising the step of adding a fragrance. In certain embodiments, the invention relates to any one of the aforementioned methods, further comprising the steps of adding a fragrance and mixing.

In certain embodiments, the invention relates to any one of the aforementioned methods, further comprising the step of adding water.

Exemplary Properties of Formulations of the Invention

In certain embodiments, the invention relates to any one of the aforementioned formulations, wherein the formulation is a cream or a foam.

In certain embodiments, the invention relates to any one of the aforementioned formulations that, upon application to the skin of an affected subject, is non-irritating.

In certain embodiments, the invention relates to any one of the aforementioned formulations that, upon application to the skin of an affected subject, is well-tolerated.

In certain embodiments, the invention relates to any one of the aforementioned formulations that, upon application to the skin of an affected subject, is non-cytotoxic.

In certain embodiments, the invention relates to any one of the aforementioned formulations that, upon application to the skin of an affected subject, is weakly sensitizing. In certain embodiments, the invention relates to any one of the aforementioned formulations that, upon application to the skin of an affected subject, is non-sensitizing.

In certain embodiments, the invention relates to any one of the aforementioned formulations that, upon application to the skin of an affected subject, does not produce edema or erythema.

In certain embodiments, the invention relates to any one of the aforementioned formulations that, upon application to the skin of an affected subject, is as effective as a reference product, wherein the reference product was made by a different method. In certain embodiments, the invention relates to any one of the aforementioned formulations that, upon application to the skin of an affected subject, is more effective than a reference product, wherein the reference product was made by a different method.

In certain embodiments, the invention relates to any one of the aforementioned formulations that, upon application to the skin of an affected subject, is as effective as a reference product, wherein the reference product has twice the quantity of hydroquinone and was made by a different method. In certain embodiments, the invention relates to any one of the aforementioned formulations that, upon application to the skin of an affected subject, is more effective than a reference product, wherein the reference product has twice the quantity of hydroquinone and was made by a different method.

In certain embodiments, the invention relates to any one of the aforementioned formulations that, upon application to the skin of affected subjects, shows improvement from baseline after 4 weeks in overall photodamage in at least about 50% of the subjects. In certain embodiments, the invention relates to any one of the aforementioned formulations that, upon application to the skin of affected subjects, shows improvement from baseline after 4 weeks in overall photodamage in at least about 50%, about 51%, about 52%, about 53%, about 54%, or about 55% of the subjects. In certain embodiments, the invention relates to any one of the aforementioned formulations that, upon application to the skin of affected subjects, shows improvement from baseline after 4 weeks in overall photodamage in about 50%, about 51%, about 52%, about 53%, about 54%, or about 55% of the subjects. In certain embodiments, the invention relates to any one of the aforementioned formulations that, upon application to the skin of affected subjects, shows improvement from baseline after 12 weeks in overall photodamage in at least about 90% of the subjects. In certain embodiments, the invention relates to any one of the aforementioned formulations that, upon application to the skin of affected subjects, shows improvement from baseline after 12 weeks in overall photodamage in at least about 90%, about 91%, about 92%, about 93%, about 94%, or about 95% of the subjects. In certain embodiments, the invention relates to any one of the aforementioned formulations that, upon application to the skin of affected subjects, shows improvement from baseline after 12 weeks in overall photodamage in about 90%, about 91%, about 92%, about 93%, about 94%, or about 95% of the subjects.

In certain embodiments, the invention relates to any one of the aforementioned formulations that, upon application to the skin of affected subjects, shows improvement from baseline after 12 weeks in mottled pigmentation in at least about 95% of the subjects. In certain embodiments, the invention relates to any one of the aforementioned formulations that, upon application to the skin of affected subjects, shows improvement from baseline after 12 weeks in mottled pigmentation in at least about 95%, about 96%, about 97%, about 98%, or about 99% of the subjects. In certain embodiments, the invention relates to any one of the aforementioned formulations that, upon application to the skin of affected subjects, shows improvement from baseline after 12 weeks in mottled pigmentation in about 95%, about 96%, about 97%, about 98%, or about 99% of the subjects.

In certain embodiments, the invention relates to any one of the aforementioned formulations that, upon application to the skin of affected subjects, shows improvement from baseline after 12 weeks in color in at least about 96% of the subjects. In certain embodiments, the invention relates to any one of the aforementioned formulations that, upon application to the skin of affected subjects, shows improvement from baseline after 12 weeks in color in at least about 96%, about 97%, about 98%, or about 99% of the subjects. In certain embodiments, the invention relates to any one of the aforementioned formulations that, upon application to the skin of affected subjects, shows improvement from baseline after 12 weeks in color in about 96%, about 97%, about 98%, or about 99% of the subjects.

In certain embodiments, the invention relates to any one of the aforementioned formulations that, upon application to the skin of affected subjects, shows an average of at least about 9% improvement from baseline after 4 weeks in overall photodamage. In certain embodiments, the invention relates to any one of the aforementioned formulations that, upon application to the skin of affected subjects, shows an average of at least about 18% improvement from baseline after 12 weeks in overall photodamage.

In certain embodiments, the invention relates to any one of the aforementioned formulations that, upon application to the skin of affected subjects, shows an average of at least about 10% improvement from baseline after 4 weeks in mottled pigmentation. In certain embodiments, the invention relates to any one of the aforementioned formulations that, upon application to the skin of affected subjects, shows an average of at least about 25% improvement from baseline after 12 weeks in mottled pigmentation.

In certain embodiments, the invention relates to any one of the aforementioned formulations that, upon application to the skin of affected subjects, shows an average of at least about 9% improvement from baseline after 4 weeks in color. In certain embodiments, the invention relates to any one of the aforementioned formulations that, upon application to the skin of affected subjects, shows an average of at least about 23% improvement from baseline after 12 weeks in color.

In certain embodiments, the invention relates to any one of the aforementioned formulations that, upon application to the skin of affected subjects, shows an average reported irritation no more than mild after 4 weeks. In certain embodiments, the invention relates to any one of the aforementioned formulations that, upon application to the skin of affected subjects, no more than 20% of subjects report irritation after 4 weeks.

In certain embodiments, the invention relates to any one of the aforementioned formulations that, upon application to the skin of affected subjects, shows an average reported irritation no more than mild after 12 weeks. In certain embodiments, the invention relates to any one of the aforementioned formulations that, upon application to the skin of affected subjects, no more than 16% of subjects report irritation after 12 weeks.

In certain embodiments, the invention relates to any one of the aforementioned formulations that, upon application to the skin of affected subjects, 100% of subjects report satisfaction levels of good, very good, or excellent after 4 weeks.

In certain embodiments, the invention relates to any one of the aforementioned formulations that, upon application to the skin of affected subjects, 100% of subjects report satisfaction levels of good, very good, or excellent after 12 weeks.

Exemplary Formulations of the Invention for Particular Uses

In certain embodiments, the invention relates to any one of the formulations for use in the treatment of a skin disorder.

In certain embodiments, the skin disorder is hyperpigmentation, photodamage, mottled pigmentation, erythema, uneven texture, or fine lines.

Exemplary Methods of Use

In certain embodiments, the invention relates to a method of treating a skin disorder, comprising the steps of:

applying topically to a subject in need thereof a therapeutically-effective amount of any one of the aforementioned formulations.

In certain embodiments, the invention relates to any one of the aforementioned methods, wherein the formulation is applied once daily or twice daily.

In certain embodiments, the invention relates to any one of the aforementioned methods, wherein the subject is human.

In certain embodiments, the invention relates to any one of the aforementioned methods, wherein the method is a method of lightening or whitening the skin of the subject.

In certain embodiments, the invention relates to any one of the aforementioned methods, wherein the skin disorder is hyperpigmentation, photodamage, mottled pigmentation, erythema, uneven texture, or fine lines.

EXEMPLIFICATION

The invention now being generally described, it will be more readily understood by reference to the following examples which are included merely for purposes of illustration of certain aspects and embodiments of the present invention, and are not intended to limit the invention.

Example 1—Compositions and Method of Manufacture

An example product concentrate (NB1238-21) was manufactured by the procedure outlined below:

Using an argon blanket over the containers, the following steps were performed:

Phase A Preparation:
1. Weigh BHT, stearyl glycyrrhetinate, cetyl alcohol, ceteth-20, steareth-20, glyceryl stearate, PEG-75 stearate, cetostearyl alcohol, *jojoba* esters, isonoyl isononanoate, C12-C15 alkyl ethylhexanoate, *moringa* butter, *moringa* oil, tocopheryl acetate, tetrahexadecyl ascorbate, bisabolol, dimethicone, dimethicone/divinyldimethicone/silsesquioxane crosspolymer, black raspberry seed oil, cranberry seed oil, pomegranate seed oil, watermelon seed oil, raspberry seed oil, and chia seed oil into a glass beaker.
2. Heat and mix to 75° C. and hold at 75° C. with continuous mixing with a spatula until transferred into main batch at 75° C.

Phase B:
1. In a glass beaker B add water at room temperature.
2. Place beaker under the homogenizer and while mixing rapidly sprinkle in magnesium aluminum silicate being careful to avoid lumps.
3. Homogenize phase B for 5 minutes.

Phase C:
1. At room temperature weigh pentylene glycol and xanthan gum into a beaker.
2. Mix until all the xanthan gum is fully wetted out and lump free.
3. Add phase C to Phase B and mix for 15 minutes until fully hydrated on the lightning mixer.

Phase D:
1. Individually add allantoin, sodium hyaluronate, panthenol, potassium sorbate, sodium benzoate, disodium EDTA, citric acid and niacinamide to Phase BC at room temperature.
2. Then heat and mix phase BCD to 75° C.
3. Making sure that phase A is at 75° C. and continuously mixing transfer phase A into phase BCD at 75° C.
4. Once fully transferred homogenize the batch for 3 minutes.
5. Move the batch to the lightning mixer and cool the batch to 35° C. (no water bath).

Phase E:
1. At 35° C. individually add algae extract, mugwort (*Artemisia vulgaris*) extract, water, glycerin and *avena sativa* (Oat) kernel extract to the batch and mix until uniform.

Phase F:
1. In a small beaker combine water, sodium bisulfite and sodium sulfite at room temperature.
2. Mix until all of the solids are completely dissolved.
3. Then add to batch at 35° C. and mix until uniform.

Phase G:
1. In a beaker weigh out pentylene glycol and chlorphenesin.
2. Heat and mix to 50° C. and mix until all of the chlorphenesin is dissolved.
3. Add to batch at 35° C.

Phase H:
1. Add water, dextran and hexapeptide-2 when batch is at 35° C.
2. Mix thoroughly and cool batch to 32° C.

Phase I:
1. In a beaker combine water, pentylene glycol and alpha-arbutin and mix thoroughly.
2. Mix until dissolved then add to the batch at 30° C.-32° C.

Phase J:
1. In a beaker combine water, pentylene glycol and kojic acid and mix thoroughly.
2. Mix until all of the Kojic Acid is suspended then add to the batch at 30° C.-32° C.

Phase K:
1. Add cyclomethicone, water, glycerin, *brassica napus* extract, *palmaria palmata* extract, *saccharomyces/xylinum*/black tea ferment and 1-methylhydantoine-2-imide individually to batch when batch is cooled to 30° C.

Phase L:
1. Weigh out pentylene glycol and licorice root extract into a beaker and mix thoroughly.
2. Add to batch at 30° C.

Phase M:
1. In a beaker weigh out pentylene glycol, water and hydroquinone.
2. Mix until all of the Hydroquinone is dispersed.
3. Add to the batch when batch is at 30° C.

Phase N:
1. Add Fragrance. Mix thoroughly.
2. QS with water

Following manufacturing of the product concentrate, the finished product was filled into containers under an inert atmosphere as outlined below.

Airless Pumps:
1. Airless pump tubes are cleaned with compressed air and vacuum
2. Product concentrate is filled into tubes
3. Tubes purged with inert gas
4. Tubes sealed with airless pump actuator.

Aerosol Cans:
1. Aerosol cans are cleaned with compressed air and vacuum.
2. Product Concentrate is filled into cans.
3. Cans are purged with inert gas.
4. Valves are placed onto the cans.
5. Cans are crimped and hydrofluorocarbon propellant is charged through diptube.

Propellant concentrations range from 8-15% by weight of packaged product.

See FIG. 1 for exemplary formulations of the invention made by the procedure described in Example 1.

Example 2—Efficacy Assessment of a 2% Hydroquinone Formulation of the Invention Versus a Commercial 4% Hydroquinone Product A twenty-five (25) subject clinical trial comparing the efficacy, tolerability and satisfaction with hydroquinone-based cosmetic products was performed. The study was of 12 weeks duration and featured a split face paired comparison design. Of the 25 subjects enrolled, 22 successfully completed the study. Efficacy assessments were performed by a panel of three physicians while tolerability and satisfaction were rated by the subjects.

Physician Evaluation of Efficacy:
As can be seen from FIG. 2, the 4% hydroquinone commercial product and the 2% hydroquinone formulation of the method exhibited equivalent percentages of subjects showing improvement from baseline. There was a slight numerical advantage demonstrated by the 2% hydroquinone formulation in the areas of overall photodamage, pigmentation mottled and improved color.

As can be seen from FIG. 3, the 4% hydroquinone commercial product and the 2% hydroquinone formulation of the method exhibited equivalent percent improvement from baseline.

Subject's Rating Regarding Irritation and Satisfaction:
Facial irritation was self-assessed using the following scoring scale:
0=None
1=Mild
2=Moderate 3=Significant
4=Severe As can be seen from FIG. 4 and FIG. 5, the 2% hydroquinone formulation of the method exhibited a lower percentage of subjects; reporting irritation at weeks 4-14 than the 4% hydroquinone commercial product.

Satisfaction with the tested treatments was self-assessed using the following scoring scale:
6=Excellent
5=Very Good
4=Good
3=Fair
2=Poor
1=Unacceptable As can be seen from FIG. 6, the 4% hydroquinone commercial product and the 2% hydroquinone formulation of the method exhibited equivalent subject satisfaction.

Example 3—Chemical Stability of Hydroquinone in Formulations of the Invention

Hydroquinone stability was demonstrated for formulations of the method. Samples were placed under conditions of elevated temperature and humidity 30° C. (86° F.)/65% relative humidity and 40° C. (104° F.)/75% relative humidity and the quantity of hydroquinone measured after 1 month. It was surprisingly discovered that under these conditions formulations of the method lost none of their initial concentration of hydroquinone at the elevated temperatures. See FIG. 7.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for decreasing the irritancy of a 1%-3% hydroquinone-containing formulation comprising adding an emollient and an anti-irritant to the formulation, wherein the formulation comprises an oil-in-water emulsion, thereby forming a less irritating hydroquinone-containing formulation, wherein the less irritating hydroquinone-containing formulations consists essentially of, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 3% to about 7% |
| Niacinamide | From about 2% to about 6% |
| Isononyl Isononoate | From about 1% to about 4% |
| $C_{12}$-$C_{15}$ Alkyl Ethylhexanoate | From about 1% to about 4% |
| Glycerin | From about 1% to about 3% |
| Hydroquinone | From about 1% to about 3% |
| Alpha-Arbutin | From about 1% to about 3% |
| Dimethicone/Divinyldimethicone/Silsesquioxane Crosspolymer | From about 1% to about 3% |
| Moringa Oleifera Seed Oil | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (Artemisia vulgaris) Extract | From about 0.5% to about 1.5% |
| Magnesium Aluminum Silicate | From about 0.5% to about 1.5% |
| PEG- 75 Stearate | From about 0.5% to about 1.5% |
| Avena Sativa (Oat) Kernel Extract | From about 0.1% to about 1.0% |
| Saccharomyces/Xylinum/Black Tea Ferment | From about 0.2% to about 0.6% |
| Palmaria Palmata Extract | From about 0.1% to about 0.4% |
| Brassica Napus Extract | From about 0.3% to about 1.0% |
| Punica Granatum (Pomegranate) Seed Oil | From about 0.1% to about 0.4% |
| Rubus Occidentalis (Black Raspberry) Seed Oil | From about 0.1% to about 0.4% |
| Vaccinium Macrocarpon (Cranberry) Seed Oil | From about 0.1% to about 0.4% |
| Citrullus Lanatus (Watermelon) Seed Oil | From about 0.01% to about 0.05% |
| Rubus Idaeus (Raspberry) Seed Oil | From about 0.01% to about 0.05% |
| Salvia Hispanica (Chia) Seed Oil | From about 0.01% to about 0.05% |
| Tetrahexadecyl Ascorbate | From about 0.3% to about 0.7% |
| Ceteth-20 | From about 0.2% to about 0.6% |
| Steareth-20 | From about 0.2% to about 0.6% |
| Allantoin | From about 0.3% to about 0.7% |
| Chlorphenesin | From about 0.1% to about 0.4% |
| Hexapeptide-2 | From about 0.1% to about 1.0% |
| Jojoba Esters | From about 0.1% to about 0.4% |
| Moringa Oil/Hydrogenated Moringa Oil Esters | From about 0.1% to about 0.4% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.05% to about 0.15% |
| Xanthan Gum | From about 0.05% to about 0.15% |
| Citric Acid | From about 0.1% to about 0.3% |
| Potassium Sorbate | From about 0.1% to about 0.3% |
| Sodium Benzoate | From about 0.1% to about 0.3% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.01% to about 0.10% |
| Hydroxyethylcellulose | From about 0.1% to about 1.0% |
| Glycyrrhiza Glabra (Licorice) Root Extract | From about 0.02% to about 0.07%. |

2. The method of claim 1, wherein the less irritating hydroquinone-containing formulation, upon application to the skin of an affected subject, does not produce edema or erythema.

3. The method of claim 1, wherein the less irritating hydroquinone-containing formulation, upon application to the skin of affected subjects, shows an average reported irritation no more than mild after 4 weeks.

4. The method of claim 1, wherein the less irritating hydroquinone-containing formulation, upon application to the skin of affected subjects, no more than 20% of subjects report irritation after 4 weeks.

5. The method of claim 1, wherein the less irritating hydroquinone-containing formulation, upon application to the skin of affected subjects, shows an average reported irritation no more than mild after 12 weeks.

6. The method of claim 1, wherein the less irritating hydroquinone-containing formulation, upon application to the skin of affected subjects, no more than 16% of subjects report irritation after 12 weeks.

7. A method for decreasing the irritancy of a 1%-3% hydroquinone-containing formulation comprising adding an emollient and an anti-irritant to the formulation, wherein the formulation comprises an oil-in-water emulsion, thereby forming a less irritating hydroquinone-containing formulation, wherein the less irritating hydroquinone-containing formulations consists essentially of, by weight of the formulation

| | |
|---|---|
| Purified Water | From about 30% to about 70% |
| Hydrofluorocarbon 227ea | From about 6% to about 18% |
| Pentylene Glycol | From about 3% to about 7% |
| Cyclomethicone | From about 1% to about 2% |
| Niacinamide | From about 2% to about 6% |
| Isononyl Isononoate | From about 1% to about 3% |
| C12-C15 Alkyl Ethylhexanoate | From about 1% to about 3% |
| Glycerin | From about 1% to about 3% |
| Hydroquinone | From about 1% to about 3% |
| Alpha-Arbutin | From about 1% to about 3% |
| Dimethicone/Divinyldimethicone/ Silequioxane Crosspolymer | From about 1% to about 3% |
| Glyceryl Stearate | From about 1% to about 3% |
| Cetyl Alcohol | From about 1% to about 3% |
| Dimethicone | From about 0.5% to about 1.5% |
| Cetearyl Alcohol | From about 0.5% to about 1.5% |
| Kojic Acid | From about 0.5% to about 1.5% |
| Panthenol | From about 0.5% to about 1.5% |
| 1-Methylhydantoine-2-Imide | From about 0.5% to about 1.5% |
| Algae Extract and Mugwort (*Artemisia vulgaris*) Extract | From about 0.5% to about 1.5% |
| Magnesium Aluminum Silicate | From about 0.5% to about 1.5% |
| PEG- 75 Stearate | From about 0.5% to about 1.5% |
| *Avena Sativa* (Oat) Kernel Extract | From about 0.1% to about 1.0% |
| *Saccharomyces/Xylinum*/Black Tea Ferment | From about 1% to about 4% |
| Palmaria Palmata Extract | From about 0.1% to about 0.5% |
| *Brassica Napus* Extract | From about 0.04% to about 0.1% |
| *Punica Granatum* (Pomegranate) Seed Oil | From about 0.3% to about 0.9% |
| *Rubus Occidentalis* (Black Raspberry) Seed Oil | From about 0.3% to about 0.9% |
| *Vaccinium Macrocarpon* (Cranberry) Seed Oil | From about 0.3% to about 0.9% |
| *Citrullus Lanatus* (Watermelon) Seed Oil | From about 0.06% to about 0.13% |
| *Rubus Idaeus* (Raspberry) Seed Oil | From about 0.06% to about 0.13% |
| *Salvia Hispanica* (Chia) Seed Oil | From about 0.06% to about 0.13% |
| Tetrahexadecyl Ascorbate | From about 0.2% to about 0.7% |
| Ceteth-20 | From about 0.1% to about 0.5% |
| Steareth-20 | From about 0.1% to about 0.5% |
| Allantoin | From about 0.2% to about 0.7% |
| Chlorphenesin | From about 0.1% to about 0.5% |
| Hexapeptide-2 | From about 0.1% to about 1.0% |
| Bisabolol | From about 0.1% to about 0.3% |
| Fragrance | From about 0.1% to about 0.3% |
| Sodium Bisulfite | From about 0.02% to about 0.07% |
| Sodium Sulfite | From about 0.02% to about 0.07% |
| Tocopheryl Acetate | From about 0.2% to about 0.7% |
| Xanthan Gum | From about 0.05% to about 0.15% |
| Citric Acid | From about 0.05% to about 0.20% |
| Potassium Sorbate | From about 0.05% to about 0.20% |
| Sodium Benzoate | From about 0.05% to about 0.20% |
| Dextran | From about 0.1% to about 1.0% |
| Sodium Hyaluronate | From about 0.005% to about 0.015% |
| BHT | From about 0.1% to about 0.3% |
| Stearyl Glycyrrhetinate | From about 0.05% to about 0.15% |
| Disodium EDTA | From about 0.05% to about 0.15% |
| Phenoxyethanol | From about 0.05% to about 0.1% |
| Hydroxyethylcellulose | From about 0.1% to about 1.0% |
| *Glycyrrhiza Glabra* (Licorice) Root Extract | From about 0.02% to about 0.07% |
| *Acacia Decurrens*/Jojoba/ Sunflower Seed Wax Polyceryl-3 Esters | From about 1% to about 3% |
| *Butyrospermum Parkii* (Shea) Butter | From about 1% to about 3%. |

8. The method of claim 7, wherein the less irritating hydroquinone-containing formulation, upon application to the skin of an affected subject, does not produce edema or erythema.

9. The method of claim 7, wherein the less irritating hydroquinone-containing formulation, upon application to the skin of affected subjects, shows an average reported irritation no more than mild after 4 weeks.

10. The method of claim 7, wherein the less irritating hydroquinone-containing formulation, upon application to the skin of affected subjects, no more than 20% of subjects report irritation after 4 weeks.

11. The method of claim 7, wherein the less irritating hydroquinone-containing formulation, upon application to the skin of affected subjects, shows an average reported irritation no more than mild after 12 weeks.

12. The method of claim 7, wherein the less irritating hydroquinone-containing formulation, upon application to the skin of affected subjects, no more than 16% of subjects report irritation after 12 weeks.

* * * * *